(12) United States Patent
Yoshida et al.

(10) Patent No.: US 9,550,732 B2
(45) Date of Patent: Jan. 24, 2017

(54) SALT OF PYRROLIDIN-3-YL ACETIC ACID DERIVATIVE AND CRYSTALS THEREOF

(71) Applicant: Eisai R&D Management Co., Ltd., Tokyo (JP)

(72) Inventors: Kenshi Yoshida, Tsukuba (JP); Ikuo Kushida, Tsukuba (JP)

(73) Assignee: Eisai R&D Management Co., Ltd., Tokyo (JP)

(*) Notice: Subject to any disclaimer, the term of this patent is extended or adjusted under 35 U.S.C. 154(b) by 0 days.

(21) Appl. No.: 14/768,520

(22) PCT Filed: Mar. 10, 2014

(86) PCT No.: PCT/JP2014/056123
§ 371 (c)(1),
(2) Date: Aug. 18, 2015

(87) PCT Pub. No.: WO2014/142056
PCT Pub. Date: Sep. 18, 2014

(65) Prior Publication Data
US 2016/0002165 A1    Jan. 7, 2016

(30) Foreign Application Priority Data

Mar. 12, 2013    (JP) ................................. 2013-049619

(51) Int. Cl.
*C07D 211/58*    (2006.01)
*C07D 401/12*    (2006.01)
*C07C 59/50*    (2006.01)

(52) U.S. Cl.
CPC ............. *C07D 211/58* (2013.01); *C07C 59/50* (2013.01); *C07D 401/12* (2013.01)

(58) Field of Classification Search
CPC ...... C07D 211/58; C07D 401/12; C07C 59/50
See application file for complete search history.

(56) References Cited

U.S. PATENT DOCUMENTS

| | | | |
|---|---|---|---|
| 8,476,301 B2 * | 7/2013 | Yoshida | C07D 403/12 514/326 |
| 2005/0143372 A1 | 6/2005 | Ghosh et al. | |
| 2007/0142386 A1 | 6/2007 | Nordvall et al. | |
| 2009/0124637 A1 | 5/2009 | Nordvall et al. | |
| 2010/0210633 A1 | 8/2010 | Lin et al. | |
| 2010/0317618 A1 | 12/2010 | Guglielmotti et al. | |
| 2013/0065925 A1 | 3/2013 | Yoshida et al. | |

FOREIGN PATENT DOCUMENTS

| | | |
|---|---|---|
| CN | 1856499 | 11/2006 |
| CN | 101193898 | 6/2008 |
| CN | 101959866 | 1/2011 |
| CN | 103764648 | 4/2014 |
| EP | 2757103 | 7/2014 |
| JP | 2002-345454 | 12/2002 |
| JP | 2007-507494 | 3/2007 |
| JP | 2008-535834 | 9/2008 |
| JP | 2011-513371 | 4/2011 |
| WO | WO 2005/033115 | 4/2005 |
| WO | 2006/107257 | 10/2006 |
| WO | 2006/107258 | 10/2006 |
| WO | 2008/039138 | 4/2008 |
| WO | 2008/039139 | 4/2008 |
| WO | WO 2009/109654 | 9/2009 |
| WO | 2009/120140 | 10/2009 |
| WO | 2013/039057 | 3/2013 |

OTHER PUBLICATIONS

International Search Report for PCT/JP2014/056123 dated Apr. 1, 2014.
Kobayashi et al., "Exclusive Increase of CX3CR1+CD28−CD4+T Cells in Inflammatory Bowel Disease and Their Recruitment as Intraepithelial Lymphocytes", Inflamm. Bowel Dis. 13(7):837-846 (2007).
Umehara et al., "Fractalkine in Vascular Biology", Arterioscler. Thromb. Vasc. Biol., vol. 24, pp. 34-40, (2004).
International Preliminary Report on Patentability in International Application No. PCT/JP2014/056123, dated Sep. 24, 2015, 6 pages.
Office Action in JP App. Ser. No. 2015-505455, dated Nov. 17, 2015, 7 pages (with English translation).
Notice of Allowance in JP App. Ser. No. 2015-505455, dated Jan. 5, 2016, 6 pages (with English translation).
Office Action in IL App. Ser. No. 240795, dated Dec. 7, 2015, 5 pages (with English translation).
Chinese Office Action in Application No. 201480012170.X, dated May 31, 2016, 11 pages, with English tmnslation.
European Search Report in Application No. 14762496.9, dated Aug. 8, 2016, 8 pages.
Israeli Submission Documents in Application No. 240795, dated Mar. 30, 2016, 4 pages, with English tmnslation.

* cited by examiner

*Primary Examiner* — D M Seaman
(74) *Attorney, Agent, or Firm* — Fish & Richardson P.C.

(57) ABSTRACT

An organic carboxylic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid and a crystal thereof.

6 Claims, 6 Drawing Sheets

SALT OF PYRROLIDIN-3-YL ACETIC ACID DERIVATIVE AND CRYSTALS THEREOF

TECHNICAL FIELD

The present invention relates to a salt of a pyrrolidin-3-yl acetic acid derivative having an inhibitory action in a fractalkine-CX3CR1 pathway, and a crystal thereof.

BACKGROUND ART

Chemokines are major cell migration factors and regulate infiltration of lymphocytes into tissues through the enhancement of cell movement and the activation of adhesion molecules. Chemokines are classified into four subfamilies of CC, CXC, C and CX3C based on their sequences of the first two cysteine residues.

Fractalkine is the sole CX3C chemokine member and has distinct characteristics in its structure and functions which are not found in other chemokines. Fractalkine binds to a receptor, CX3CR1, which can mediate strong adhesion without mediation of selectin or integrin even in the presence of a physiological blood flow. This means that the fractalkine-CX3CR1 system mediates multi-stage infiltration mechanism through selectin or integrin by only a one-stage reaction.

Expression of fractalkine on vascular endothelial cells is induced by inflammatory cytokines TNF and IL-1. On the other hand, CX3CR1 is expressed on monocytes, almost all NK cells and some T cells, but is not expressed on neutrophils. Therefore, the fractalkine-CX3CR1 system is considered to be an extremely effective mechanism to mobilize immune cells onto the endothelial cells of damaged tissues or into the tissues.

With regard to the relation between the fractalkine-CX3CR1 system and pathologies, it is suggested that the fractalkine-CX3CR1 system is involved in the development and pathologies of autoimmune diseases such as rheumatoid arthritis, inflammatory bowel disease, lupus nephritis and multiple sclerosis (Non Patent Literature 1). In particular, with regard to inflammatory bowel disease, it is reported that expression of fractalkine is enhanced at inflammatory sites of colonic tissues of patients and that CX3CR1 plays an important role in the infiltration of immune cells into the colon tissue (Non Patent Literature 2).

Antibodies described in Patent Literature 1 and low molecular weight compounds described in Patent Literatures 2 to 6 have been previously known as fractalkine inhibitors.

In addition, compounds described in Patent Literature 7 are described to be useful as chemokine CCR2 receptor antagonists, but differ in the target chemokine family from such inhibitors.

CITATION LIST

Patent Literature

Patent Literature 1: Japanese Patent Application Laid-Open Publication No. 2002-345454
Patent Literature 2: WO 2006/107257
Patent Literature 3: WO 2006/107258
Patent Literature 4: WO 2008/039138
Patent Literature 5: WO 2008/039139
Patent Literature 6: WO 2009/120140
Patent Literature 7: U.S. Patent Application Laid-Open Publication No. 2010/0210633

Non Patent Literature

Non Patent Literature 1: Umehara et al., "Fractalkine in Vascular Biology", Arterioscler. Thromb. Vasc. Biol., Vol. 24, pp. 34-40, 2004
Non Patent Literature 2: Kobayashi et al., "Exclusive Increase of CX3CR1_CD28_CD4_T Cells in Inflammatory Bowel Disease and Their Recruitment as Intraepithelial Lymphocytes", Inflamm. Bowel. Dis., Vol. 13, pp. 837-846, 2007

SUMMARY OF INVENTION

Technical Problem

It is an object of the present invention to discover a compound having an inhibitory activity in a fractalkine-CX3CR1 pathway.

In addition, since the physical properties of a compound, a salt thereof, and their crystals and their amorphous forms used as a pharmaceutical product largely influence on the bioavailability of a drug, the purity of an active pharmaceutical ingredient, prescription of a preparation and the like, it needs to be studied upon the development of pharmaceutical products which form of the aforementioned compound, a salt, a crystal or an amorphous form, is most excellent as a pharmaceutical product. That is to say, it is another object of the present invention to discover a salt of a compound, their crystals, and their amorphous forms, which have usability as active pharmaceutical ingredients.

Solution to Problem

The present inventors have found that compound (1) represented by the following formula, namely, 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid has an inhibitory activity in a fractalkine-CX3CR1 pathway. Furthermore, the present inventors have isolated various types of organic carboxylic acid salts of the compound (1), their crystals, and their amorphous forms, and they have grasped the physical properties or forms thereof and have conducted various studies thereon, so that the present inventors have discovered an organic carboxylic acid salt, a crystal thereof, and an amorphous form thereof that has usability as an active pharmaceutical ingredient, thereby completing the present invention.

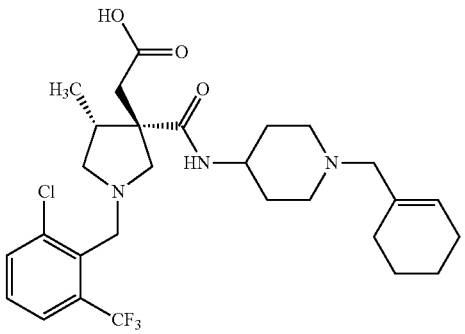 [SMILES: C[C@H]1CN(Cc2c(Cl)cccc2C(F)(F)F)C[C@@]1(CC(=O)O)C(=O)NC1CCN(CC2=CCCCC2)CC1]

Specifically, the present invention relates to:
1) an organic carboxylic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid;

2) the salt according to 1) above, which is characterized by that the organic carboxylic acid is L-mandelic acid;
3) the salt according to 1) above, which is characterized by that the organic carboxylic acid is L-lactic acid;
4) a crystal of the organic carboxylic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid;
5) the crystal according to 4) above, which is characterized by that the organic carboxylic acid is L-mandelic acid;
6) the crystal according to 4) above, which is characterized by that the organic carboxylic acid is L-lactic acid;
7) the crystal according to 5) above, which is characterized by having a diffraction peak at a diffraction angle (2θ±0.2°) of 7.2° in powder X-ray diffractometry;
8) the crystal according to 7) above, which is characterized by having further diffraction peaks at diffraction angles (2θ±0.2°) of 14.4° and 15.7° in powder X-ray diffractometry;
9) the crystal according to 8) above, which is characterized by having further diffraction peaks at diffraction angles (2θ±0.2°) of 10.3° and 23.5° in powder X-ray diffractometry;
10) the crystal according to 9) above, which is characterized by having further diffraction peaks at diffraction angles (2θ±0.2°) of 12.9°, 14.9°, 17.2°, 20.10 and 24.7° in powder X-ray diffractometry;
11) the crystal according to 5) above, which is characterized by having peaks at chemical shifts (ppm) of 14.1, 52.9, 75.2, 144.7 and 174.0 in $^{13}C$ solid state NMR spectrum;
12) the crystal (A) according to 6) above, which is characterized by having a diffraction peak at a diffraction angle (2θ±0.2°) of 6.9° in powder X-ray diffractometry;
13) the crystal (A) according to 12) above, which is characterized by having further diffraction peaks at diffraction angles (2θ±0.2°) of 15.7° and 17.1° in powder X-ray diffractometry;
14) the crystal (B) according to 6) above, which is characterized by having a diffraction peak at a diffraction angle (2θ±0.2°) of 6.8° in powder X-ray diffractometry; and
15) the crystal (B) according to 14) above, which is characterized by having further diffraction peaks at diffraction angles (2θ±0.2°) of 13.7° and 16.8° in powder X-my diffractometry.

Advantageous Effects of Invention

According to the present invention, an organic carboxylic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid that has usability as an active pharmaceutical ingredient, and a crystal thereof can be provided.

DESCRIPTION OF EMBODIMENTS

Figure 1:
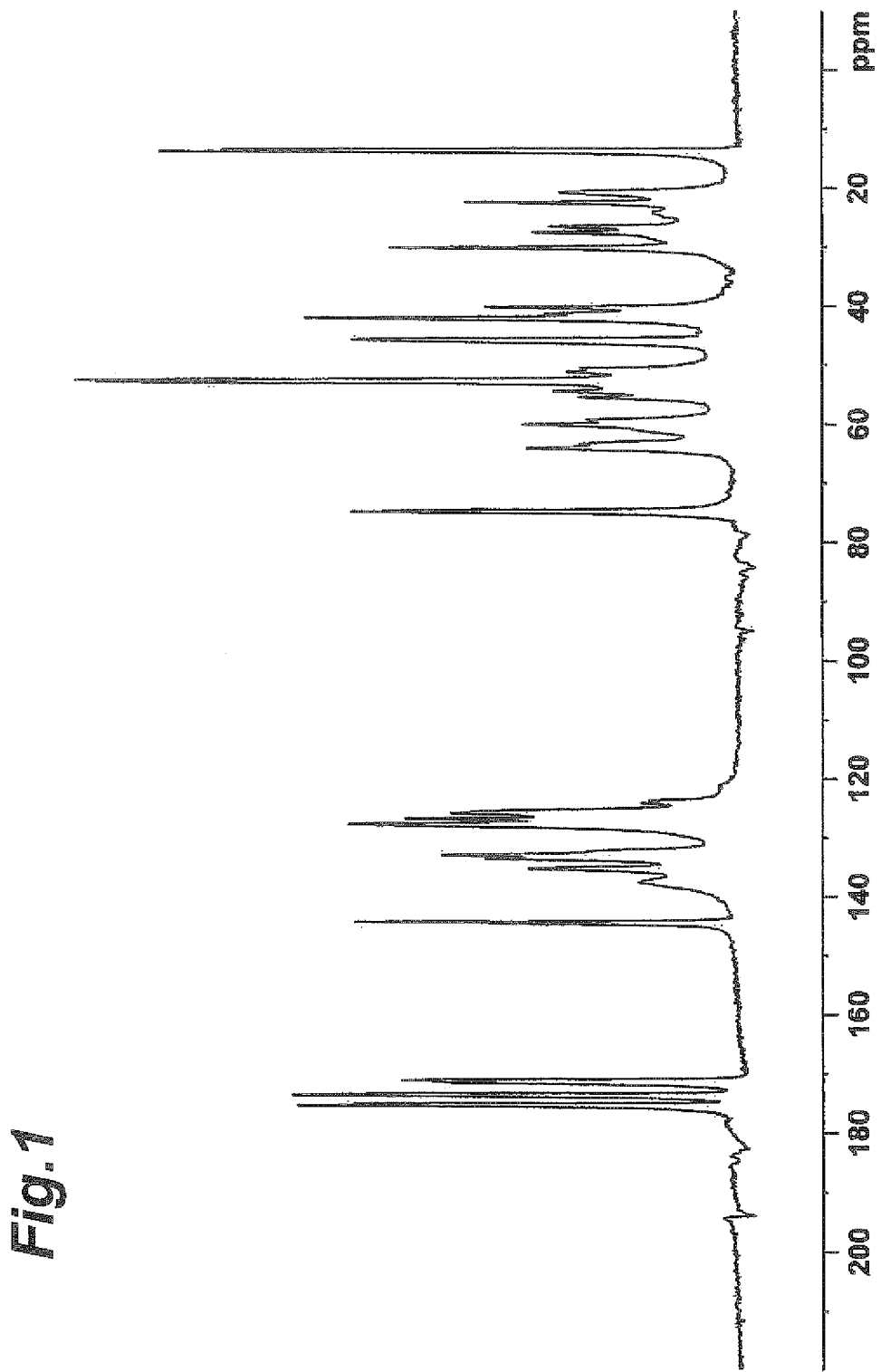
FIG. 1 shows a $^{13}C$ solid state NMR spectrum of a crystal of L-mandelic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid.

An organic carboxylic acid salt of the compound (1) of the present invention, a crystal thereof, an amorphous form thereof, and production methods thereof will be described in detail.
Compound (1), namely, 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid can be produced based on the description of the after-mentioned Production Example 1.
In the present description, the organic carboxylic acid salt of the compound (1) means a pharmaceutically acceptable salt, and this is a salt comprising one organic carboxylic acid selected from the group consisting of acetic acid, succinic acid, glutaric acid, benzoic acid, cinnamic acid, malic acid, oxalic acid, glycolic acid, maleic acid, tartaric acid, diacetyltartaric acid, fumaric acid, citric acid, malonic acid, L-lactic acid, L-mandelic acid and the like, and the compound (1). The term "salt" is used herein to mean a compound generated as a result of a reaction of the compound (1) with organic carboxylic acid having a chemically possible number of equivalent, wherein the compound consists of a positive part of bases in the molecules of the compound (1) and a negative part of the organic carboxylic acid.
Examples of the organic carboxylic acid salt include acetic acid salt, succinic acid salt, glutaric acid salt, benzoic acid salt, cinnamic acid salt, malic acid salt, oxalic acid salt, glycolic acid salt, maleic acid salt, tartric acid salt, diacetyltartric acid salt, fumaric acid salt, citric acid salt, malonic acid salt, L-lactic acid salt, and L-mandelic acid salt. Preferred examples of the organic carboxylic acid salt include oxalic acid salt, glycolic acid salt, L-lactic acid salt and L-mandelic acid salt, and more preferred examples include L-lactic acid salt and L-mandelic acid salt.

The organic carboxylic acid salt of the compound (1) may also be a solvate. In the present description, the solvate of the organic carboxylic acid salt of the compound (1) means a solid formed from the organic carboxylic acid salt of the compound (1) together with solvent molecules. Examples of the solvate include: a solvate formed from the organic carboxylic acid salt of the compound (1) together with a ketone solvent such as acetone, methyl ethyl ketone or cyclohexanone; a solvate formed from the organic carboxylic acid salt of the compound (1) together with an ester solvent such as ethyl acetate or methyl acetate; a solvate formed from the organic carboxylic acid salt of the compound (1) together with an ether solvent such as 1,2-dimethoxyethane or methyl-tert-butyl ether; a solvate formed from the organic carboxylic acid salt of the compound (1) together with an alcohol solvent such as methanol, ethanol, 1-propanol or isopropanol; a solvate formed from the organic carboxylic acid salt of the compound (1) together with a polar solvent such as 1-methyl-2-pyrrolidone, N,N-dimethylformamide or dimethyl sulfoxide; and a hydrate formed from the organic carboxylic acid salt of the compound (1) together with water.

The organic carboxylic acid salt of the compound (1) or a solvate thereof may be either a crystal or an amorphous form. Preferred specific examples of the organic carboxylic acid salt of the compound (1) or a solvate thereof include L-mandelic acid salt of the compound (1) and a solvate of L-lactic acid salt of the compound (1).

If preferred forms of the organic carboxylic acid salt of the compound (1) or a solvate thereof are further specifically described, preferred specific examples include the following crystals.

Preferred specific examples thereof include:

(a) a crystal of L-mandelic acid salt of the compound (1) characterized in that it has diffraction peaks in powder X-ray diffractometry [diffraction angle (2θ±0.2°)] at angles, for example, of
(1) 7.2°,
(2) 10.3°,
(3) 12.9°,
(4) 14.4°,
(5) 14.9°,
(6) 15.7°,
(7) 17.2°,
(8) 20.10,
(9) 23.5°, and
(10) 24.70
wherein the diffraction peaks at the angles of 7.2°, 10.3°, 14.4°, 15.7° and 23.5°, and among others, the diffraction peaks at the angles of 7.2°, 14.4° and 15.7°, and in particular, the diffraction peak at the angle of 7.2° is a peak characteristic for the present crystal, or a crystal of L-mandelic acid salt of the compound (1) characterized in that it has peaks at chemical shifts (ppm) of 14.1, 52.9, 75.2, 144.7 and 174.0 in $^{13}C$ solid state NMR spectrum;

(b) a crystal (A) of a solvate of L-lactic acid salt of the compound (1) characterized in that it has diffraction peaks in powder X-ray diffractometry [diffraction angle (2θ±0.2°)] at angles, for example, of
(1) 6.9°,
(2) 9.2°,
(3) 10.0°,
(4) 10.8°,
(5) 13.8°,
(6) 14.8°,
(7) 15.7°,
(8) 17.1°,
(9) 20.5°, and
(10) 23.80
wherein the diffraction peaks at the angles of 6.9°, 14.8°, 15.7°, 17.1° and 23.8°, and among others, the diffraction peaks at the angles of 6.9°, 15.7° and 17.1°, and in particular, the diffraction peak at the angle of 6.9° is a peak characteristic for the present crystal; and (c) a crystal (B) of a solvate of L-lactic acid salt of the compound (1) characterized in that it has diffraction peaks in powder X-ray diffractometry [diffraction angle (2θ±0.2°)] at angles, for example, of
(1) 6.8°,
(2) 10.8°,
(3) 13.7°,
(4) 15.1°,
(5) 16.8°,
(6) 18.1°,
(7) 18.9°,
(8) 23.5°,
(9) 24.70, and
(10) 25.60
wherein the diffraction peaks at the angles of 6.8°, 13.7°, 16.8°, 18.1° and 18.90, and among others, the diffraction peaks at the angles of 6.8°, 13.7° and 16.8°, and in particular, the diffraction peak at the angle of 6.8° is a peak characteristic for the present crystal.

The above described characteristic peaks in powder X-ray diffractometry are unique to each of the crystal of L-mandelic acid salt of the compound (1), the crystal of the solvate (A) of L-lactic acid salt of the compound (1), and the crystal of the solvate (B) L-lactic acid salt of the compound (1).

In general, with regard to the diffraction angle (2θ) in powder X-ray diffractometry, since errors may be generated in the range of ±0.2°, it is necessary to understand that the above described diffraction angle value includes numerical values in the range of approximately ±0.2°. Accordingly, not only a crystal in which the diffraction angle of the peak in powder X-ray diffractometry is completely identical to that in the crystal of the present invention, but also a crystal in which the diffraction angle of the peak is identical to that in the crystal of the present invention with an error of approximately ±0.2°, is included in the present invention. Therefore, for example, the phrase "having a diffraction peak at a diffraction angle (2θ±0.2°) of 7.2°" is used in the present description to mean "having a diffraction peak at a diffraction angle (2θ) of from 7.0° to 7.40°." The same applies to other cases regarding the diffraction angle (2θ) in powder X-ray diffractometry.

The above described characteristic peaks in $^{13}C$ solid state NMR spectrum are unique to the $^{13}C$ solid state NMR spectrum of the crystal of L-mandelic acid salt of the compound (1).

The description "having peaks at chemical shifts (ppm) of 14.1, 52.9, 75.2, 144.7 and 174.0" is used in the present description to mean that "a $^{13}C$ solid state NMR spectrum is measured under ordinary measurement conditions or under conditions substantially identical to those described in the present description, and as a result, the spectrum exhibits peaks substantially equivalent to those at chemical shifts (ppm) of 14.1, 52.9, 75.2, 144.7 and 174.0."

For determination regarding whether or not the spectrum exhibits "substantially equivalent peaks," since, in general, errors may be generated in the range of ±0.5 ppm with regard to the chemical shifts (ppm) in $^{13}C$ solid state NMR spectrum, it is necessary to understand that the above described chemical shift value includes numerical values in the range of approximately ±0.5 ppm. Accordingly, a crystal in which the chemical shift in $^{13}$C solid state NMR spectrum is completely identical to that in the crystal of the present invention, but also a crystal in which the chemical shift is identical to that in the crystal of the present invention with an error of approximately ±0.5 ppm, is included in the present invention. Therefore, for example, the phrase "having a peak at a chemical shift (ppm) of 14.1" is used in the present description to mean "having a peak at a chemical shift (ppm) of from 13.6 to 14.6." The same applies to other cases regarding the chemical shift in $^{13}$C solid state NMR spectrum.

Next, methods for producing L-mandelic acid salt of the compound (1), a crystal thereof, an amorphous form thereof and a solvate thereof will be described in detail. It is to be noted that other organic carboxylic acid salts of the compound (1), their crystals and their amorphous forms, or their solvates can also be produced according to the methods as described in detail below, or methods equivalent thereto. In particular, upon production of a solvate of an organic carboxylic acid salt of the compound (1), a solvent for the desired solvate needs to be added.

[Method for Producing L-Mandelic Acid Salt of the Compound (1)]

L-mandelic acid salt of the compound (1) can be obtained by a conventional method for producing an organic carboxylic acid salt. Specifically, L-mandelic acid salt of the compound (1) can be produced, for example, as follows: L-mandelic acid that has previously been dissolved in a solvent is directly added to the compound (1); or the compound (1) is dissolved in a solvent, as necessary, under heating, and thereafter, L-mandelic acid that has previously been dissolved in a solvent is added to the obtained solution, followed by stirring the obtained mixture at room temperature or while cooling in a cooling bath for approximately several minutes to 50-60 hours, or followed by leaving the mixture at room temperature or while cooling in a cooling bath for approximately several minutes to 50-60 hours. Otherwise, L-mandelic acid salt of the compound (1) can also be produced by directly adding a solvent to the compound (1) and L-mandelic acid, and then dissolving them in the solvent. By these production methods, L-mandelic acid salt of the compound (1) can be obtained in the form of a crystal or an amorphous form.

Examples of the solvent used herein include one solvent, and a mixed solvent of two or more solvents, which are selected from the group consisting of: alkylketone solvents such as acetone or methyl ethyl ketone; ethyl acetate; hexane; acetonitrile; ether solvents such as ether, methyl-tert-butyl ether or 1,2-dimethoxyethane; alcohol solvents such as ethanol, 1-propanol, isopropanol or t-butyl alcohol; and water. More preferred examples of the solvent include acetone, methyl ethyl ketone, ethyl acetate, acetone/methyl-tert-butyl ether (at a volume ratio of 1:1), ethanol/methyl-tert-butyl ether (at a volume ratio of 1:12), and isopropanol/methyl-tert-butyl ether (at a volume ratio of 1.5:8 to 1.5:13.5).

Moreover, the amount of a solvent used can be selected as appropriate, provided that the amount of a solvent in which the compound (1) and L-mandelic acid are dissolved by heating is determined as a lower limit, and that the amount of a solvent in which the yield of salts is not significantly reduced is determined as an upper limit. The ratio of the volume of the solvent to the weight of the compound (1) is preferably, for example, 5 to 100 times (v/w); and when acetone, methyl ethyl ketone, ethyl acetate, acetone/methyl-tert-butyl ether (at a volume ratio of 1:1), ethanol/methyl-tert-butyl ether (at a volume ratio of 1:12), isopropanol/methyl-tert-butyl ether (at a volume ratio of 1.5:8 to 1.5:13.5), or the like is used as a solvent, the ratio of the volume of the solvent to the weight of the compound (1) is more preferably, for example, 5 to 20 times (v/w).

The temperature, at which the compound (1) and L-mandelic acid are dissolved in a solvent, may be determined, as appropriate, depending on the used solvent. The temperature is preferably, for example, from the reflux temperature of the used solvent to 15° C., and more preferably, for example, from 15° C. to 100° C.

If a cooling rate applied during crystallization is changed, crystals having different forms (polymorphisms) may be generated. Hence, taking into consideration influence on the quality, grain size and the like of a crystal, cooling is desirably carried out, while adjusting a cooling rate, as appropriate; and cooling can be carried out preferably at a cooling rate of, for example, 5° C. to 40° C./hour, and more preferably at a cooling rate of, for example, 15° C. to 25° C./hour. Furthermore, the final crystallization temperature can be determined, as appropriate, depending on the yield, quality and the like of a crystal, and it is preferably, for example, −25° C. to 30° C.

Upon crystallization of crystals, a seed crystal (a crystal of L-mandelic acid salt of the compound (1)) may be added or may not be added. The temperature, at which such a seed crystal is added, is not particularly limited, and it is preferably, for example, 0° C. to 60° C.

The crystallized crystal is separated by an ordinary filtration operation, and the filtrated crystal is then washed with a solvent, as necessary, and the resulting crystal is further dried, so as to obtain a crystal of interest. Preferred examples of the solvent used in the washing of a crystal include acetone, methyl ethyl ketone, ethyl acetate, methyl-tert-butyl ether, acetone/methyl-tert-butyl ether (at a volume ratio of 1:1), acetone/isopropyl acetate (at a volume ratio of 1:9), and isopropanol/methyl-tert-butyl ether (at a volume ratio of 1:10); and more preferred examples of the solvent include ethyl acetate, methyl-tert-butyl ether, isopropanol/methyl-tert-butyl ether (at a volume ratio of 1:10), acetone/methyl-tert-butyl ether (at a volume ratio of 1:1), and acetone/isopropyl acetate (at a volume ratio of 1:9).

Next, a method for producing a crystal of L-mandelic acid salt of the compound (1) and a method for drying the crystal will be described more in detail. It is to be noted that crystals of other organic carboxylic acid salts of the compound (1), or crystals of their solvates can also be produced and dried according to the methods as described in detail below or methods equivalent thereto.

[Method for Crystallizing Crystal of L-Mandelic Acid Salt of Compound (1)]

A crystal of L-mandelic acid salt of the compound (1) can be crystallized as follows: after compound (1) is produced according to Production Example 1, L-mandelic acid that has previously been dissolved in a solvent is directly added to the compound (1); or the compound (1) is dissolved in a solvent, as necessary, under heating, and thereafter L-mandelic acid that has previously dissolved in a solvent is added to the obtained solution, followed by stirring the mixture at room temperature or while cooling in a cooling bath for approximately several minutes to 50-60 hours, or followed by leaving the mixture at room temperature or while cooling in a cooling bath for approximately several minutes to 50-60 hours, according to the above described [method for producing L-mandelic acid salt of the compound (1)]. Otherwise, such a crystal of L-mandelic acid salt of the compound (1) can also be produced by directly adding a solvent to the compound (1) and L-mandelic acid and dissolving them in the solvent. Alternatively, L-mandelic acid salt of the compound (1) is once obtained, and this is then dissolved in a solvent, so that a crystal can be crystallized.

A method for recrystallizing L-mandelic acid salt of the compound (1) will be described in detail below.

L-mandelic acid salt of the compound (1) used in crystallization may be an amorphous form or a crystal (including a crystal comprising of a plurality of crystalline polymorphisms), and it may also be a mixture thereof.

Preferred examples of the solvent used in crystallization include one solvent, and a mixed solvent of two or more solvents, which are selected from the group consisting of acetone, ethyl acetate, isopropyl acetate, isobutyl acetate, hexane, heptane, acetonitrile, methyl-tert-butyl ether, tetrahydrofuran, ethanol, 1-propanol, isopropanol, dimethyl sulfoxide, and water; and more preferred examples thereof include ethyl acetate, dimethyl sulfoxide/isopropyl acetate/heptane (at a volume ratio of 3:2:10), dimethyl sulfoxide/isopropyl acetate (at a volume ratio of 1:8 to 1:16), dimethyl sulfoxide/isopropanol/methyl-tert-butyl ether (at a volume ratio of 3:3:20 to 3:2:25), dimethyl sulfoxide/acetone/isopropyl acetate (at a volume ratio of 1.70:3:25), dimethyl sulfoxide/acetone/heptane (at a volume ratio of 1.65:3:25), and dimethyl sulfoxide/ethyl acetate/heptane (at a volume ratio of 2.0:10:10).

Moreover, the amount of a solvent used can be selected as appropriate, provided that the amount of a solvent in which L-mandelic acid salt of the compound (1) is dissolved by heating is determined as a lower limit, and that the amount of a solvent in which the yield of crystals is not significantly reduced is determined as an upper limit.

The ratio of the volume of the solvent to the weight of the compound (1) is preferably, for example, 5 to 100 times (v/w); and when ethyl acetate, dimethyl sulfoxide/isopropyl acetate/heptane (at a volume ratio of 3:2:10), dimethyl sulfoxide/isopropyl acetate (at a volume ratio of 1:8 to 1:16), dimethyl sulfoxide/isopropanol/methyl-tert-butyl ether (at a volume ratio of 3:3:20 to 3:2:25), dimethyl sulfoxide/acetone/isopropyl acetate (at a volume ratio of 1.70:3:25), dimethyl sulfoxide/acetone/heptane (at a volume ratio of 1.65:3:25), dimethyl sulfoxide/ethyl acetate/heptane (at a volume ratio of 2.0:10:10), or the like is used as a solvent, the ratio of the volume of the solvent to the weight of the compound (1) is more preferably, for example, 15 to 40 times (v/w).

The temperature at which L-mandelic acid salt of the compound (1) is heated and dissolved in a solvent may be determined as appropriate depending on the used solvent. The temperature is preferably, for example, from 15° C. to the reflux temperature of a solvent used for recrystallization, and more preferably, for example, from 40° C. to 100° C. If a cooling rate applied during crystallization is changed, crystals having different forms (polymorphisms) may be generated. Hence, taking into consideration influence on the quality, grain size and the like of a crystal, cooling is desirably carried out, while adjusting a cooling rate, as appropriate; and cooling can be carried out preferably at a cooling rate of, for example, 5° C. to 40° C./hour, and more preferably at a cooling rate of, for example, 15° C. to 25° C./hour. Furthermore, the final crystallization temperature can be determined, as appropriate, depending on the yield, quality and the like of a crystal, and it is preferably, for example, –25° C. to 30° C.

Upon crystallization of crystals, a seed crystal (a crystal of L-mandelic acid salt of the compound (1)) may be added or may not be added. The temperature, at which such a seed crystal is added, is not particularly limited, and it is preferably, for example, 60° C. or lower, more preferably, for example, 0° C. to 60° C., and further preferably, for example, 15° C. to 60° C.

The crystallized crystal is separated by an ordinary filtration operation, and the filtrated crystal is then washed with a solvent, as necessary, and the resulting crystal is further dried, so as to obtain a crystal of interest. Preferred examples of the solvent used in the washing of a crystal include acetone, methyl ethyl ketone, ethyl acetate, methyl-tert-butyl ether, acetone/methyl-tert-butyl ether (at a volume ratio of 1:1), isopropanol/methyl-tert-butyl ether (at a volume ratio of 1:10), and acetone/isopropyl acetate (at a volume ratio of 1:4 to 1:9); and more preferred examples thereof include ethyl acetate, methyl-tert-butyl ether, acetone/methyl-tert-butyl ether (at a volume ratio of 1:1), isopropanol/methyl-tert-butyl ether (at a volume ratio of 1:10), and acetone/isopropyl acetate (at a volume ratio of 1:9).

[Method for Drying Crystal of L-Mandelic Acid Salt of Compound (1)]

As described above, the crystal separated by a filtration operation can be dried, as appropriate, by leaving it in the air or by heating it. The time required for the drying operation is a time required until the amount of the residual solvent has become smaller than a predetermined amount, and it may be determined, as appropriate, depending on the amount of a product, a drying device, a drying temperature, and the like. Moreover, such drying can also be carried out either under ventilation or under reduced pressure. The degree of reduced pressure may be determined, as appropriate, depending on the amount of a product, a drying device, a drying temperature, and the like. After completion of the drying operation, the obtained crystal can also be left in the air, as necessary Next, a method for producing an amorphous form of the L-mandelic acid salt of the compound (1) and a method for drying the amorphous form will be described in detail. It is to be noted that amorphous forms of other organic carboxylic acid salts of the compound (1), or amorphous forms of their solvates can also be produced and dried according to the methods as described in detail below or methods equivalent thereto.

[Method for Producing Amorphous Form of L-Mandelic Acid Salt of Compound (1)]

An amorphous form of the salt of the compound (1) and L-mandelic acid can be obtained by a conventional method for producing an amorphous form. Specifically, the amorphous form can be produced as follows: the compound (1) produced in Production Example 1 is dissolved in a solvent, as necessary, under heating, and L-mandelic acid is then added thereto, followed by stirring or leaving the obtained mixture for approximately several minutes to 50-60 hours, and thereafter distilling off the solvent under reduced pressure. Otherwise, the amorphous form can also be produced by directly adding a solvent to the compound (1) and L-mandelic acid and then dissolving them in the solvent, and then distilling off the solvent under reduced pressure. Alternatively, the amorphous form can also be produced by freeze-drying L-mandelic acid salt of the compound (1) thus obtained.

Examples of the solvent used herein include one solvent, and a mixed solvent of two or more solvents, which are selected from the group consisting of: alkylketone solvents such as acetone or methyl ethyl ketone; ethyl acetate; hexane; acetonitrile; ether solvents such as ether, methyl-tert-butyl ether or 1,2-dimethoxyethane; alcohol solvents such as ethanol, 1-propanol, isopropanol or t-butyl alcohol;

and water. More preferred examples of the solvent include acetone, methyl ethyl ketone, ethyl acetate, acetone/methyl-tert-butyl ether (at a volume ratio of 1:1), ethanol/methyl-tert-butyl ether (at a volume ratio of 1:12), and isopropanol/methyl-tert-butyl ether (at a volume ratio of 1.5:8 to 1.5:13.5).

Moreover, the amount of a solvent used can be selected as appropriate, provided that the amount of a solvent in which the compound (1) and L-mandelic acid are dissolved by heating is determined as a lower limit, and that the amount of a solvent in which the yield of salts is not significantly reduced is determined as an upper limit. The ratio of the volume of the solvent to the weight of the compound (1) is preferably, for example, 5 to 100 times (v/w); and when acetone, methyl ethyl ketone, ethyl acetate, acetone/methyl-tert-butyl ether (at a volume ratio of 1:1), ethanol/methyl-tert-butyl ether (at a volume ratio of 1:12), isopropanol/methyl-tert-butyl ether (at a volume ratio of 1.5:8 to 1.5:13.5), or the like is used as a solvent, the ratio of the volume of the solvent to the weight of the compound (1) is more preferably, for example, 5 to 20 times (v/w).

The temperature at which the compound (1) and L-mandelic acid are dissolved in a solvent may be selected as appropriate from temperatures at which the compound (1) and organic carboxylic acid are dissolved in a solvent, depending on the used solvent. The temperature is preferably, for example, from 15° C. to the reflux temperature of the solvent used, and more preferably, for example, from 15° C. to 100° C.

An amorphous form of the L-mandelic acid salt of the compound (1) can be obtained by distilling off the solvent under reduced pressure from the solution thus obtained. Moreover, an amorphous form of the L-mandelic acid salt of the compound (1) which is excellent in solubility can be obtained by freeze-drying the obtained L-mandelic acid salt of the compound (1), using one solvent or a mixed solvent of two or more solvents selected from the group consisting of alcohol solvents such as ethanol, 1-propanol, isopropanol or t-butyl alcohol, ether solvents such as dioxane, polar solvents such as dimethyl sulfoxide, and water, or preferably using, for example, water, t-butyl alcohol, dioxane or dimethyl sulfoxide.

[Method for Drying Amorphous Form of L-Mandelic Acid Salt of Compound (1)]

The thus obtained amorphous form can be dried, as appropriate, by leaving it in the air or by heating it. The time required for the drying operation is a time required until the amount of the residual solvent has become smaller than a predetermined amount, and it may be determined, as appropriate, depending on the amount of a product, a drying device, a drying temperature, and the like. Moreover, such drying can also be carried out either under ventilation or under reduced pressure. The degree of reduced pressure may be determined, as appropriate, depending on the amount of a product, a drying device, a drying temperature, and the like. After completion of the drying operation, the obtained amorphous form can also be left in the air, as necessary.

The organic carboxylic acid salt of the compound (1) has an inhibitory action in a fractalkine-CX3CR1 pathway, and has usability as an active ingredient of therapeutic agents for inflammatory bowel diseases such as ulcerative colitis or Crohn's disease.

When the organic carboxylic acid salt of the compound (1) is used as a pharmaceutical agent, it can be orally or parenterally administered, for example, as a therapeutic agent for inflammatory bowel diseases such as ulcerative colitis or Crohn's disease, which are caused by fractalkine-CX3CR1. The dose of the pharmaceutical agent of the present invention is generally different depending on symptoms, age, sex, body weight, etc., and it may be an amount sufficient for exhibiting a desired effect. For example, when the subject is an adult, the pharmaceutical agent is administered at a dose of approximately 0.1 to 5000 mg (preferably 0.5 to 1000 mg, and more preferably 1 to 600 mg) per day, for one or several days, once or divided over 2 to 6 administrations per day.

The organic carboxylic acid salt of the compound (1) can be formulated by conventional methods, and examples of dosage forms include oral formulations (such as tablets, granules, powders, capsules and syrups), injections (for intravenous administration, intramuscular administration, subcutaneous administration and intraperitoneal administration) and external formulations (such as transdermal absorption formulations (such as ointments and patches), ophthalmic preparations, nasal preparations and suppositories).

When a solid preparation for oral administration is produced, an excipient, a binder, a disintegrator, a lubricant, a coloring agent and the like are added, as necessary, to the organic carboxylic acid salt of the compound (1), and a tablet, a granule, a powder agent, or a capsule can be produced according to a conventional method. Moreover, such a tablet, a granule, a powder agent, a capsule or the like may be subjected to film coating, as necessary.

Examples of the excipient include lactose, corn starch, and crystalline cellulose; examples of the binder include hydroxypropyl cellulose and hydroxypropylmethyl cellulose; examples of the disintegrator include carboxymethyl cellulose calcium and croscarmellose sodium; examples of the lubricant include magnesium stearate and calcium stearate; examples of the coloring agent include titanium oxide; and examples of the film coating agent include hydroxypropyl cellulose, hydroxypropylmethyl cellulose, and methyl cellulose, but naturally, examples of the additives are not limited thereto.

A solid preparation such as a tablet, a capsule, a granule or a powder agent may comprise the organic carboxylic acid salt of the compound (1) in an amount of generally, for example, 0.001% to 99.5% by weight, and preferably 0.001% to 90% by weight.

When injections (for intravenous administration, intramuscular administration, subcutaneous administration and intraperitoneal administration) are manufactured, they can be manufactured by adding pH adjusters, buffers, suspending agents, solubilizing agents, antioxidants, preservatives (antiseptics), tonicity adjusting agents or the like to the organic carboxylic acid salt of the compound (1) as necessary and treating by conventional methods. Lyophilized formulations to be dissolved before use may also be prepared by lyophilization. These injections can be administered intravenously, subcutaneously and intramuscularly, for example.

Examples of pH adjusters and buffers include organic acids or inorganic acids and/or salts thereof examples of suspending agents include methylcellulose, polysorbate 80 and carboxymethylcellulose sodium, examples of solubilizing agents include polysorbate 80 and polyoxyethylene sorbitan monolaurate, examples of antioxidants include α-tocopherol, examples of preservatives include methyl parahydroxybenzoate and ethyl parahydroxybenzoate, and examples of tonicity adjusting agents include glucose, sodium chloride and mannitol; however, the excipients are not limited to these examples, obviously.

These injections may contain usually 0.000001 to 99.5 wt %, preferably 0.00001 to 90 wt % or the like, of the organic carboxylic acid salt of the compound (1).

When an external agent is produced, a base material is added to the organic carboxylic acid salt of the compound (1), and as necessary, for example, the above described preservative, stabilizer, pH adjuster, antioxidant, and coloring agent are added thereto, and thereafter, according to a conventional method, for example, a percutaneous absorption preparation (an ointment, a patch, etc.), an eye drop, a nasal drop, a suppository, and the like can be produced.

As base materials used, various types of raw materials that are commonly used in pharmaceutical products, quasi-drugs, cosmetic products, etc. can be used. Specifically, examples of the base material include raw materials such as animal and vegetable oils, mineral oil, ester oil, waxes, emulsifier, higher alcohols, fatty acids, silicon oil, surfactant, phospholipids, alcohols, polyhydric alcohols, water-soluble polymers, clay minerals, and purified water.

These external formulations may contain usually 0.000001 to 99.5 wt %, preferably 0.00001 to 90 wt % or the like, of the organic carboxylic acid salt of the compound (1).

EXAMPLE

Hereinafter, the present invention will be described in detail with the production examples and examples. However, the present invention is not intended to be limited by these examples.

Production Example 1

Preparation of 2-[(3S,4R)-1-{[2-Chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid Production Example 1a Benzyl(2E)-but-2-enoate Crotonic acid (70 g, 812 mmol) was dissolved in N,N-dimethylformamide (467 ml), which was cooled in an ice bath under nitrogen, and potassium carbonate (61.6 g, 447 mmol) was added. Benzyl bromide (91.7 ml, 772 mmol) was added dropwise to the reaction mixture over 20 minutes. The reaction mixture was stirred at room temperature for 18 hours. Ethyl acetate was added to the reaction mixture, which was filtered through Celite. The filtered ethyl acetate solution was washed with water, a saturated aqueous sodium bicarbonate solution and a saturated aqueous sodium chloride solution. The organic layer was dried over magnesium sulfate, filtered and concentrated under reduced pressure to give the title compound (142 g, yield: 99.4%).

$^1$H-NMR (400 MHz, CDCl$_3$) δ (ppm): 1.87-1.90 (3H, m), 5.17 (2H, s), 5.87-5.92 (1H, m), 6.98-7.07 (1H, m), 7.26-7.39 (5H, m).

Production Example 1b

Benzyl(3RS,4SR)-1-benzyl-4-methlpyrrolidine-3-carboxylate

Benzyl(2E)-but-2-enoate obtained in Production Example 1a (20.5 g, 116 mmol) was dissolved in dichloromethane (5 ml), and the mixture was cooled in an ice bath with stirring. Trifluoroacetic acid (257 μl, 3.47 mmol) was added, and N-(methoxymethyl)-N-(trimethylsilylmethyl)benzylamine (33.1 g, 139 mmol) was added dropwise to the reaction liquid over 15 minutes so that the internal temperature did not exceed 62° C., while washing with dichloromethane (25 ml). The reaction liquid was left to stand until it reached room temperature and was stirred for 15 hours. The reaction liquid was concentrated and purified by silica gel column chromatography (elution solvent: ethyl acetate/heptane) to give the title compound (38 g).

$^1$H-NMR (400 MHz, CDCl$_3$) δ (ppm): 1.14 (3H, d, J=6 Hz), 2.18-2.22 (1H, m), 2.48-2.65 (2H, m), 2.75-2.85 (2H, m), 2.90-2.94 (1H, m), 3.54-3.66 (2H, m), 5.13 (2H, s), 7.20-7.40 (10H, m).

Production Example 1c

Benzyl(3RS,4SR)-1-benzyl-3-[2-(tert-butoxy)-2-oxoethyl]-4-methylpyrrolidine-3-carboxylate Benzyl(3RS,4SR)-1-benzyl-4-methylpyrrolidine-3-carboxylate obtained in Production Example 1b (30 g, 97.4 mmol) was dissolved in tetrahydrofuran (300 ml), which was cooled to −70° C. with stirring under nitrogen. A 1.11 M lithium diisopropylamide/n-hexane-tetrahydrofuran solution (105 ml, 116 mmol) was added dropwise over 20 minutes so that the internal temperature did not exceed −64.3° C. The mixture was stirred at −70° C. for 1 hour, and tetrahydrofuran (30 ml) and tert-butyl bromoacetate (26.6 g, 136 mmol) were then added dropwise over 10 minutes so that the internal temperature did not exceed −60° C. The reaction mixture was stirred at −70° C. for further one hour, and a saturated aqueous ammonium chloride solution was then added to the reaction mixture. Immediately thereafter, the reaction mixture was diluted with water and ethyl acetate was added. The organic layer was washed with brine and a 5 N aqueous hydrochloric acid solution, and then dried over magnesium sulfate, filtered and concentrated. The residue was purified by silica gel column chromatography (elution solvent: ethyl acetate/heptane). The residue was further purified by NH silica gel column chromatography (elution solvent: heptane/ethyl acetate=98/2) to give the title compound (6 g, yield: 14.5%).

$^1$H-NMR (400 MHz, CDCl$_3$) δ (ppm): 0.86 (3H, d, J=6 Hz), 1.34 (9H, s), 2.05-2.15 (2H, m), 2.53 (1H, d, J=17 Hz), 2.91-3.00 (3H, m), 3.28 (1H, d, J=10 Hz), 3.59-3.72 (2H, m), 5.08-5.16 (2H, m), 7.19-7.39 (10H, m).

18.1 g of the title compound was obtained by the same method as that described above.

Production Example 1d 1,3-Dibenzyl(3RS,4SR)-3-[2-(tert-butoxy)-2-oxoethyl]-4-methylpyrrolidine-1,3-dicarboxylate Benzyl(3RS,4SR)-1-benzyl-3-[2-(tert-butoxy)-2-oxoethyl]-4-methylpyrrolidine-3-carboxylate obtained in a manner similar to that in Production Example 1c (11.7 g, 27.6 mmol) was dissolved in dichloromethane (117 ml), and benzyl chloroformate (23.7 ml, 166 mmol) was added dropwise to the reaction liquid over 20 minutes so that the internal temperature did not exceed 22° C. The mixture was stirred at room temperature for 12 hours, and then solvent was distilled off. The residue was purified by NH silica gel column chromatography (elution solvent: ethyl acetate/heptane) to give the title compound (9.1 g, yield: 70.5%).

$^1$H-NMR (400 MHz, CDCl$_3$) δ ppm; 0.84-0.90 (3H, m), 1.32-1.46 (9H, m), 2.09-2.16 (1H, m), 2.21-2.27 (1H, m), 3.04-3.14 (2H, m), 3.33-3.38 (1H, m), 3.60-3.68 (1H, m), 4.32 (1H, t, J=12 Hz), 5.07-5.20 (4H, m), 7.26-7.36 (10H, m).
Analysis by HPLC;
(Analysis conditions 1) Column: CHIRALPAK AD-H (manufactured by Daicel Chemical Industries, Ltd.) (0.46 cm diameter×15 cm), eluent: hexane/ethanol=95/5 (v/v), flow rate: 1 ml/min., detection: UV (210 nm)
(Analysis result) The resulting title compound was analyzed under the above analysis conditions 1, and a peak with a retention time of 8.56 minutes and a peak with a retention time of 10.85 minutes were observed.
The title compound separately obtained was analyzed in a chiral column different from the above column.
(Analysis conditions 2) Column: CHIRALPAK IA (manufactured by Daicel Chemical Industries, Ltd.) (0.46 cm diameter×15 cm), eluent: hexane/ethanol=95/5 (v/v), flow rate: 1 m/min., detection: UV (210 nm)
(Analysis result) The resulting title compound was analyzed under the above analysis conditions 2, and a peak with a retention time of 6.78 minutes and a peak with a retention time of 8.20 minutes were observed.

Production Example 1e (3S,4R)-3-[2-(tert-Butoxy)-2-oxoethyl]-4-methylpyrrolidine-3-carboxylic acid 1,3-Dibenzyl(3RS,4SR)-3-[2-(tert-butoxy)-2-oxoethyl]-4-methylpyrrolidine-1,3-dicarboxylate obtained in Production Example 1d (9.1 g) was optically resolved repeatedly under the following two types of conditions A or B.
Optical resolution by HPLC;
(Fractionation conditions A) Column: CHIRALPAK AD-H (manufactured by Daicel Chemical Industries, Ltd.) (2 cm diameter×25 cm), eluent: hexane/ethanol=85/15 (v/v), flow rate: 8-10 ml/min.
(Fractionation conditions B) Column: CHIRALPAK IA (manufactured by Daicel Chemical Industries, Ltd.) (3 cm diameter×25 cm), eluent: hexane/ethanol=95/5 (v/v), flow rate: 22 ml/min.
The peak with a shorter retention time was fractionated, and the resulting three lots were then analyzed under the following analysis conditions.
Analysis by HPLC;
(Analysis conditions) Column: CHIRALPAK AD-H (manufactured by Daicel Chemical Industries, Ltd.) (0.46 cm diameter×15 cm), eluent: hexane/ethanol=95/5 (v/v), flow rate: 1 ml/min., detection: UV (210 nm)
(Analysis result) The retention time was 9.0 minutes to 9.3 minutes, and the enantiomeric excess was >99% ee for all lots.
The three lots were combined, the resulting chiral form (4.04 g) was dissolved in methanol (121 ml), 10% Pd/C (0.77 g) was added, and the atmosphere was replaced with hydrogen gas. The mixture was stirred at room temperature for 13 hours and then stirred with addition of warm water (30 to 40° C., 122 ml), and the precipitated solid was dissolved. After Pd/C was filtered off, the solvent was concentrated and dried to give the title compound (2.1 g).
$^1$H-NMR (400 MHz, D$_2$O) δ ppm; 0.97 (3H, d, J=7 Hz), 1.42 (9H, s), 2.15-2.22 (1H, m), 2.30 (1H, d, J=17 Hz), 2.93 (1H, d, J=17 Hz), 3.04 (1H, t, J=12 Hz), 3.18 (1H, d, J=12 Hz), 3.49 (1H, dd, J=8, 12 Hz), 4.03 (1H, d, J=12 Hz).

Each chemical shift indicates a value that is corrected by setting the chemical shift of a solvent residual peak in heavy water at 4.79.

Production Example 1f (3S,4R)-1-Benzyl-3-[2-(tert-butoxy)-2-oxoethyl]-4-methylpyrrolidine-3-carboxylic acid A mixture of (3R*,4S*)-3-[2-(tert-butoxy)-2-oxoethyl]-4-methylpyrrolidine-3-carboxylic acid obtained in Production Example 1e (1.8 g, 7.4 mmol), benzaldehyde (1.51 ml, 14.8 mmol), acetic acid (0.635 ml, 11.1 mmol), sodium triacetoxyborohydride (3.14 g, 14.8 mmol) and methanol (35 ml) was heated at 40° C. for 38 hours and 30 minutes. The reaction mixture was concentrated, and the resulting residue was purified by silica gel column chromatography (ODS silica gel, elution solvent: water/methanol) to give the title compound as Lot A (584 mg) and Lot B (708 mg).
$^1$H-NMR (400 MHz, CDCl$_3$) of Lot A δ ppm; 1.02 (3H, d, J=7 Hz), 1.38 (9H, s), 2.14 (1H, d, J=17 Hz), 2.15-2.28 (1H, br), 2.97 (1H, d, J=17 Hz), 3.10-3.42 (3H, m), 4.00-4.10 (1H, m), 4.30-4.40 (1H, br), 4.46 (1H, d, J=12 Hz), 7.45-7.53 (5H, m).
$^1$H-NMR of Lot B: identical to NMR of Lot A.

Production Example 1g tert-Butyl 4-[(3S,4R)-1-benzyl-3-[2-(tert-butoxy)-2-oxoethyl]-4-methylpyrrolidin-3-amide]piperidine-1-carboxylate tert-Butyl 4-aminopiperidine-1-carboxylate (849 mg, 4.24 mmol), triethylamine (1.18 ml, 8.48 mmol) and PyBOP (2.21 g, 4.24 mmol) were added to a solution of (3R*,4S*)-1-benzyl-3-[2-(tert-butoxy)-2-oxoethyl]-4-methylpyrrolidine-3-carboxylic acid obtained by a method similar to that of Production Example 1f (942 mg, 2.83 mmol) in N,N-dimethylformamide (20 ml), followed by stirring at room temperature overnight. Ethyl acetate was added to the reaction liquid, which was washed with a 1 N aqueous sodium hydroxide solution and brine. This was dried over anhydrous magnesium sulfate and concentrated. The residue was purified by silica gel column chromatography (elution solvent: heptane/ethyl acetate) to give the title compound (1.33 g, yield: 91.1%/o).
$^1$H-NMR (400 MHz, CDCl$_3$) δ (ppm): 0.92 (3H, d, J=7 Hz), 1.20-1.40 (2H, m), 1.40 (9H, s), 1.48 (9H, s), 1.78-1.88 (1H, m), 1.92-1.98 (1H, m), 1.96 (1H, d, J=16 Hz), 2.03-2.09 (1H, m), 2.36 (1H, d, J=10 Hz), 2.58-2.68 (2H, m), 2.89-2.95 (2H, m), 3.10 (1H, d, J=16 Hz), 3.59 (1H, d, J=10 Hz), 3.66 (2H, s), 3.83-4.00 (3H, m), 7.23-7.35 (5H, m), 8.65 (1H, d, J=7 Hz).
MS (ESI) m/z: 538.2 (M+Na)$^+$.

Production Example 1h tert-Butyl 4-[(3S,4R)-3-[2-(tert-butoxy)-2-oxoethyl]-4-methylpyrrolidin-3-amide]piperidine-1-carboxylate 20% palladium hydroxide (724 mg) was added to a solution of tert-butyl 4-[(3R*,4S*)-1-benzyl-3-[2-(tert-butoxy)-2-oxoethyl]-4-methylpyrrolidin-3-amido]piperidine-1-carboxylate obtained in Production Example 1g (1.33 g, 2.58 mmol) in methanol (30 ml), which was stirred under a hydrogen atmosphere overnight. The reaction liquid was filtered and concentrated under reduced pressure to give the title compound (1.04 g, yield: 94.7%).

¹H-NMR (400 MHz, CDCl₃) δ (ppm): 0.92 (3H, d, J=7 Hz), 1.20-1.52 (2H, m), 1.41 (9H, s), 1.43 (9H, s), 1.80-2.10 (5H, m), 2.00 (1H, d, J=16 Hz), 2.55-2.61 (1H, m), 2.80-3.06 (2H, m), 2.92 (1H, d, J=10 Hz), 3.12 (1H, d, J=16 Hz), 3.35 (1H, d, J=9 Hz), 3.70 (1H, d, J=10 Hz), 3.80-4.00 (3H, m), 8.30 (1H, d, J=7 Hz).

MS (ESI m/z: 426.1 (M+H)⁺

Production Example 1i tert-Butyl 4-[(3S,4R)-3-[2-(tert-butoxy)-2-oxoethyl]-1-{[2-chloro-6-(trifluoromethyl)phenyl]methyl}-4-methylpyrrolidin-3-amido]piperidine-1-carboxylate 2-(Bromomethyl)-1-chloro-3-(trifluoromethyl)benzene (443 mg, 1.62 mmol) and potassium carbonate (244 mg) were added to a solution of tert-butyl 4-[(3R*,4S*)-3-[2-(tert-butoxy)-2-oxoethyl]-4-methylpyrrolidin-3-amido]piperidine-1-carboxylate obtained in Production Example 1h (345 mg, 0.811 mmol) in N,N-dimethylformamide (dehydrated) (10 mL), which was stirred at 45° C. for six hours and at 40° C. for two days. Ethyl acetate was added to the reaction liquid, which was washed with a 1 N aqueous sodium hydroxide solution and brine. This was dried over anhydrous magnesium sulfate and concentrated. The residue was purified by silica gel column chromatography (elution solvent: heptane/ethyl acetate) to give the title compound (320 mg, yield: 63.8%).

¹H-NMR (400 MHz, CDCl₃) δ (ppm): 0.92 (3H, d, J=7 Hz), 1.13-1.18 (2H, m), 1.39 (9H, s), 1.49 (9H, s), 1.53-1.65 (1H, m), 1.76-1.86 (1H, m), 1.98 (1H, d, J=16 Hz), 2.02-2.10 (1H, m), 2.51 (11H, d, J=10 Hz), 2.60-2.80 (3H, m), 2.88 (1H, t, J=10 Hz), 3.12 (1H, d, J=16 Hz), 3.53 (1H, d, J=10 Hz), 4.09-4.25 (5H, m), 7.38 (1H, t, J=8 Hz), 7.63 (2H, d, J=8 Hz), 7.96 (1H, d, J=8 Hz).

MS (ESI m/z: 640.2 (M+Na).

Production Example 1j

2-[(3S,4R)-1-{[2-Chloro-6-(trifluoromethyl)phenyl]methyl}-4-methyl-3-[(piperidin-4-yl)carbamoyl]pyrrolidin-3-yl]acetic acid Trifluoroacetic acid (8 mL) was added to a solution of tert-butyl 4-[(3R*,4S*)-3-[2-(tert-butoxy)-2-oxoethyl]-1-{[2-chloro-6-(trifluoromethyl)phenyl]methyl}-4-methylpyrrolidin-3-amido]piperidine-1-carboxylate obtained in Production Example 1i (320 mg, 0.518 mmol) in dichloromethane (dehydrated) (8 mL) under ice-cooling, followed by stirring at room temperature for 2.5 hours. The reaction liquid was concentrated under reduced pressure, and the residue was purified by ODS column chromatography (elution solvent: water/methanol) to give a mixture containing the title compound (344 mg).

¹H-NMR (400 MHz, CD₃OD) δ (ppm): 0.83 (3H, d, J=5 Hz), 1.43-1.63 (2H, m), 1.76-1.89 (1H, m), 1.92-2.00 (1H, m), 2.03-2.19 (2H, m), 2.55-2.68 (2H, m), 2.91-3.10 (4H, m), 3.25-3.36 (2H, m), 3.45-3.59 (1H, m), 3.75-4.18 (3H, m), 7.41-7.76 (3H, m).

MS (ESI) m/z: 462.3 (M+H)⁺

Production Example 1k

2-[(3S,4R)-1-{[2-Chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid Cyclohex-1-ene-1-carbaldehyde (423 μl, 3.73 mmol), acetic acid (300 μl) and sodium triacetoxyborohydride (789 mg 3.73 mmol) were added to a solution of the mixture of 2-[(3R*,4S*)-1-{[2-chloro-6-(trifluoromethyl)phenyl]methyl}-4-methyl-3-[(piperidin-4-yl)carbamoyl]pyrrolidin-3-yl]acetic acid obtained by the method of Production Example 1j (344 mg, 0.745 mmol) in tetrahydrofuran (dehydrated) (10 mL), followed by stirring overnight. Water and methanol were added to the reaction liquid, which was concentrated under reduced pressure, and the residue was purified by ODS column chromatography (elution solvent: water/methanol). The purified product was dissolved in dichloromethane, suspended by adding hexane and concentrated to give the title compound (180 mg, yield: 43.4%).

¹H-NMR (400 MHz, CD₃OD) δ (ppm): 0.89 (3H, d, J=7 Hz), 1.23-1.38 (2H, m), 1.44-1.82 (6H, m), 1.82-1.96 (1H, m), 1.96-2.25 (5H, m), 2.30-2.45 (2H, m), 2.55-2.68 (2H, m), 2.92-3.20 (5H, m), 3.54 (1H, d, J=10 Hz), 3.64-3.78 (1H, m), 3.95 (1H, d, J=10 Hz), 4.05 (1H, d, J=10 Hz), 5.76 (1H, s), 7.47-7.52 (1H, m), 7.72 (1H, d, J=7 Hz), 7.77 (1H, d, J=8 Hz).

MS (ESI) m/z: 578.3 (M+Na)+

Example 1

Preparation of Crystal of L-Mandelic Acid Salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid An ethyl acetate solution of L-mandelic acid (20 mg/mL) was added in an amount of 1407 μL (1 equivalent) to 2-[(3S,4R)-1-{[2-chloro-6-(trifluoromethyl)phenyl]methyl}-3-{[1-(cyclohex-1-en-1-ylmethyl) piperidin-4-yl] carbamoyl}-4-methylpyrrolidin-3-yl]acetic acid (102.8 mg), and the obtained mixed solution was then subjected to an ultrasonic treatment, and thereafter, the mixed solution was stirred with a magnetic stirrer at room temperature. After the mixed solution had been stirred overnight, since a solid was found in the solution, the solid was collected by filtration, and it was washed with ethyl acetate and was then dried to obtain the title crystal (49.3 mg).

¹H-NMR (600 MHz, CD₃OD) δ (ppm): 0.90 (3H, d, J=7 Hz), 1.58-1.64 (2H, m), 1.64-1.76 (4H, m), 1.82-1.89 (1H, m), 1.97-2.07 (3H, m), 2.08-2.14 (2H, m), 2.19 (1H d, d, J=17 Hz), 2.15-2.23 (1H, m), 2.62 (1H, d, J=10 Hz), 2.67 (1H, dd, J=10, 7 Hz), 2.72-2.84 (2H, m), 3.00 (1H, dd, J=10, 10 Hz), 3.10 (1H, d, J=17 Hz), 3.25-3.32 (2H, m), 3.43 (2H, s), 3.53 (1H, d, J=10 Hz), 3.77-3.85 (1H, m), 3.98 (1H, d, J=13 Hz), 4.07 (1H, d, J=13 Hz), 4.91 (1H, s), 5.91 (1H, brds), 7.23 (1H, t, J=7 Hz), 7.29 (2H, dd, J=7, 7 Hz), 7.46 (2H, d, J=7 Hz), 7.51 (1H, dd, J=8, 8 Hz), 7.73 (1H, d, J=8 Hz), 7.79 (1H, d, J=8 Hz).

The ¹³C solid state NMR spectrum of the crystal of L-mandelic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]

acetic acid obtained by the above described method was measured under the following conditions.

[Measurement Conditions]
Device used: AVANCE 400 (manufactured by BRUKER)
Measurement temperature: room temperature (22° C.)
Standard substance: glycine (external standard: 176.03 ppm)
Measurement nucleus: $^{13}$C (100.6248425 MHz)
Pulse repetition time: 6 seconds
Pulse mode: TOSS measurement The measured $^{13}$C solid state NMR spectrum is shown in FIG. 1, and the chemical shift is shown below.

$^{13}$C-NMR (100 MHz, solid state) δ (ppm): 13.8, 14.1, 21.0, 22.8, 24.3, 26.8, 27.8, 30.5, 40.5, 41.6, 42.4, 46.0, 50.9, 51.4, 52.9, 53.3, 54.7, 55.7, 59.5, 60.3, 63.6, 64.4, 75.2, 124.0, 124.4, 126.2, 127.2, 128.1, 133.3, 133.9, 135.5, 137.8, 144.7, 171.5, 174.0, 175.5, 175.8.

Figure 2:
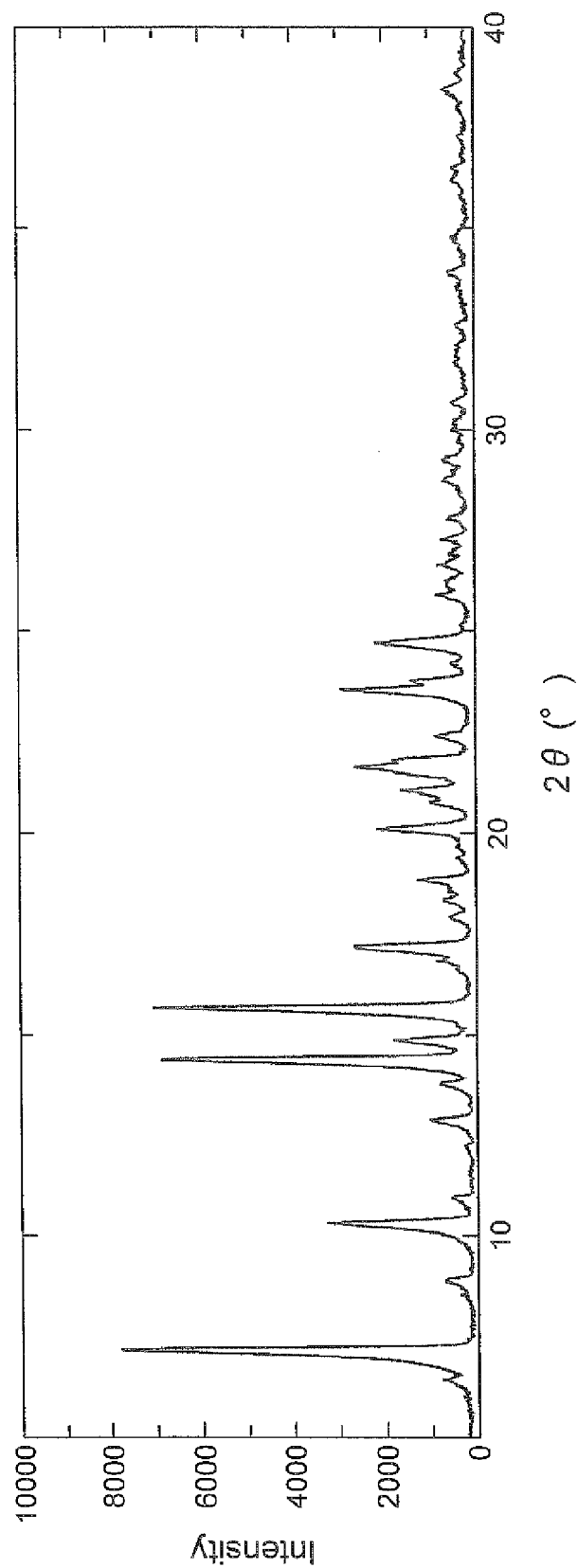
FIG. 2 shows a powder X-ray diffraction pattern of a crystal of L-mandelic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid. The abscissa indicates diffraction angle 2θ, and the ordinate indicates peak intensity.

The crystal of L-mandelic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid obtained by the above described method was placed on a sample stage of a powder X-ray ditffactometer, and it was then analyzed under the following measurement conditions. The obtained powder X-ray diffraction pattern is shown in FIG. 2.

TABLE 1

Measurement conditions

| | |
|---|---|
| Target | Copper |
| Detector | Scintillation counter |
| Tube voltage | 50 kV |
| Tube current | 300 mA |
| Slit | Divergence slit 0.5 mm, scattering slit open, receiving slit open |
| Scan rate | 5°/min |
| Sampling interval | 0.02 |
| Scan range | 5°-35° |
| Sample holder | Holder made of aluminum |

Example 2

Preparation of Amorphous Form of L-Mandelic Acid Salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid L-mandelic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl] acetic acid (53.61 mg) was weighed, and it was then placed in a 200-mL beaker, and then, tert-butyl alcohol (tBA) (20 mL) and water (4 mL) were added to the beaker. A 100-mL egg-plant flask (recovery flask) was rotated, while it was immersed in ethanol cooled with dry ice. The sample solution was added dropwise into the flask, and was then frozen. After the total amount of the sample solution had been frozen, the opening of the flask was covered with a wiping cloth and it was then freeze-dried. Thus, 48.60 mg of the title amorphous form was obtained.

$^1$H-NMR (600 MHz, CD$_3$OD) δ (ppm): 0.90 (3H, d, J=7 Hz), 1.58-1.64 (2H, m), 1.64-1.76 (4H, m), 1.82-1.90 (1H, m), 1.98-2.07 (3H, m), 2.08-2.15 (2H, m), 2.15-2.23 (1H, m), 2.19 (1H, m), 2.62 (1H, d, J=10 Hz), 2.67 (1H, dd, J=10, 7 Hz), 2.74-2.85 (2H, m), 3.00 (1H, dd, J=10, 10 Hz), 3.10 (1H, d, J=17 Hz), 3.25-3.33 (2H, m), 3.44 (2H, s), 3.53 (1H, d, J=10 Hz), 3.78-3.85 (1H, m), 3.98 (1H, d, J=13 Hz), 4.07 (1H, d, J=13 Hz), 4.91 (1H, s), 5.91 (1H, brds), 7.23 (1H, t, J=7 Hz), 7.29 (2H, dd, J=7, 7 Hz), 7.46 (2H, d, J=7 Hz), 7.51 (1H, dd, J=8, 8 Hz), 7.73 (1H, d, J=8 Hz), 7.79 (1H, d, J=8 Hz).

Figure 3:
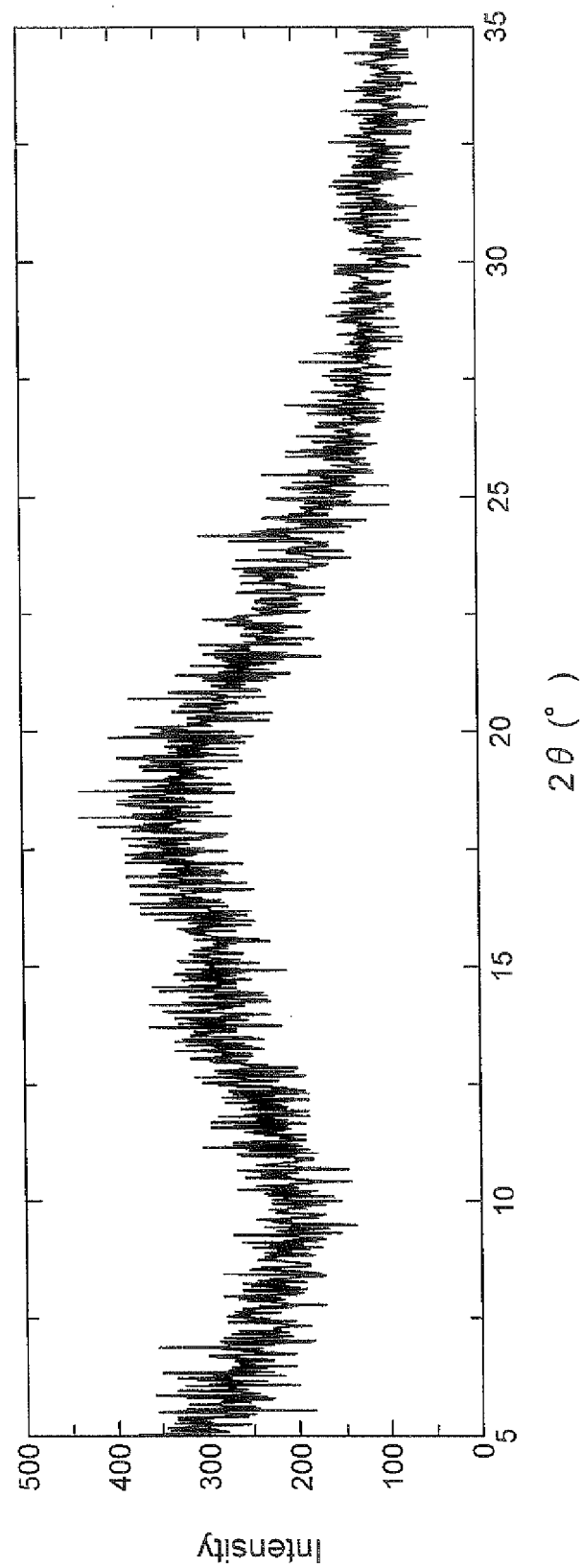
FIG. 3 shows a powder X-ray diffraction pattern of an amorphous form of L-mandelic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid. The abscissa indicates diffraction angle 2θ, and the ordinate indicates peak intensity.

The amorphous form obtained by the above described method was placed on a sample stage of a powder X-ray diffractometer, and it was then analyzed under the measurement conditions described in Example 1. The obtained powder X-ray diffraction pattern is shown in FIG. 3.

Example 3

Preparation of Crystal of Solvate (A) of L-Lactic Acid Salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid An ethyl acetate solution of L-lactic acid (10 mg/mL) was added in an amount of 1296 μL (1 equivalent) to 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid (81.38 mg), and the obtained solution was then subjected to an ultrasonic treatment, and thereafter, the reaction solution was stirred with a magnetic stirrer at room temperature. Since a solid was found in the solution, the solid was collected by filtration, and it was washed with ethyl acetate and was then dried to obtain the title crystal (78.93 mg).

Figure 4:
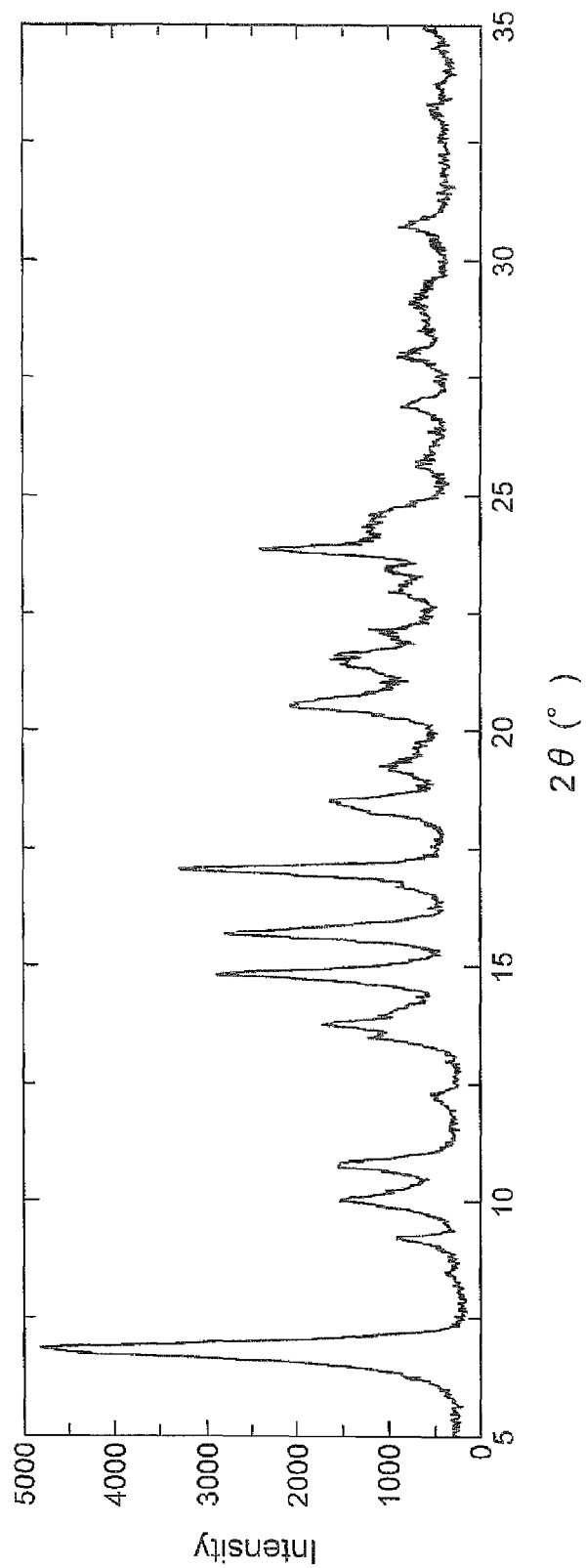
FIG. 4 shows a powder X-ray diffraction pattern of a crystal (A) of a solvate of L-lactic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid. The abscissa indicates diffraction angle 2θ, and the ordinate indicates peak intensity.

The crystal of the solvate of L-lactic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid obtained by the above described method was placed on a sample stage of a powder X-ray diffractometer, and it was then analyzed under the measurement conditions described in Example 1. The obtained powder X-ray diffraction pattern is shown in FIG. 4.

Example 4

Preparation of Crystal of Solvate (B) of L-Lactic Acid Salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid A methyl ethyl ketone solution of L-lactic acid (10 mg/mL) was added in an amount of 1318 μL (1 equivalent) to 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid (79.99 mg), and the obtained solution was then subjected to an ultrasonic treatment, and thereafter, the reaction solution was stirred with a magnetic stirrer at room temperature. Since a solid was found in the solution, the solid was collected by filtration, and it was washed with methyl ethyl ketone and was then dried to obtain the title crystal (67.56 mg).

Figure 5:
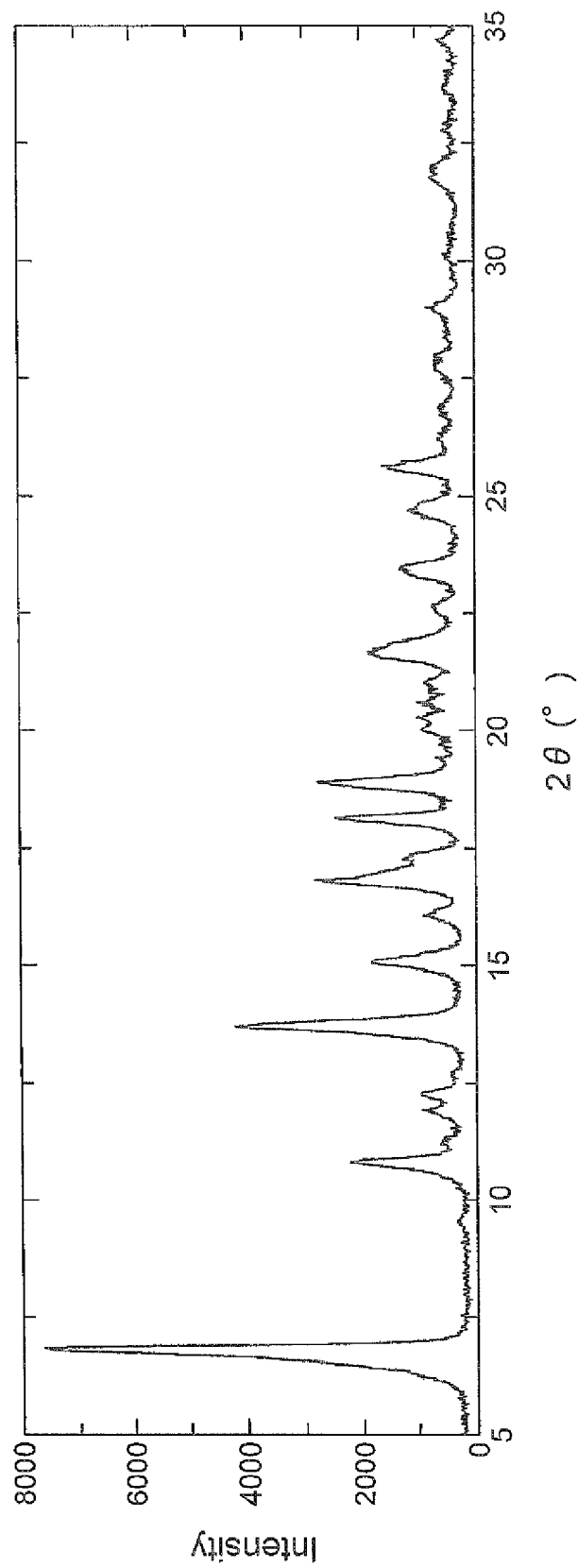
FIG. 5 shows a powder X-ray diffraction pattern of a crystal (B) of a solvate of L-lactic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid. The abscissa indicates diffraction angle 2θ, and the ordinate indicates peak intensity.

The crystal of the solvate of L-lactic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid obtained by the above described method was placed on a sample stage of a powder X-ray diffractometer, and it was then analyzed under the measurement conditions described in Example 1. The obtained powder X-ray diffraction pattern is shown in FIG. 5.

Example 5

Preparation of Crystal of L-Mandelic Acid Salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid L-mandelic acid (60.2 mg) dissolved in a mixed solvent of acetone (0.5 mL) and methyl-tert-butyl ether (0.5 mL) was added dropwise to 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl] acetic acid (230 mg content: 200 mg) dissolved in a mixed solvent of acetone (0.75 mL) and methyl-tert-butyl ether (0.75 mL), and further, the obtained mixture was then washed with a mixed solvent of acetone (0.25 mL) and methyl-tert-butyl ether (0.25 mL). The reaction mixture was stirred at room temperature for two nights. Thereafter, the obtained crystal was filtrated, and was then washed with acetone/methyl-tert-butyl ether (at a volume ratio of 1:1) (0.4 mL×3) and methyl-tert-butyl ether (0.4 mL×3), so as to obtain 223.0 mg of the title crystal (yield: 88%) in the form of a white crystal.

Example 6

Recrystallization of L-Mandelic Acid Salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid Dimethyl sulfoxide (1.65 mL) and acetone (2.0 mL) were added to a crystal of L-mandelic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid (1.00 g), and the crystal was dissolved therein by heating the mixture at 60° C. Further, dimethyl sulfoxide (0.05 mL) and acetone (1.0 mL) were further added to the obtained solution. To the obtained solution, isopropyl acetate (10 mL) was added, and after completion of the addition, the resulting solution was heated at 45° C. Then, isopropyl acetate (15 mL) was further added to the reaction solution at 45° C. The obtained solution was cooled to −20° C., and thereafter, the generated crystal was filtrated and was then washed with a mixed solvent of acetone/isopropyl acetate (at a volume ratio of 1:9, 5 mL), and the resultant was then dried at ordinary temperature, so as to obtain 907.1 mg of the title crystal (yield: 90.7%) in the form of a white crystal.

Example 7

X-Ray Crystallography of L-Mandelic Acid Salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid L-mandelic acid salt of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl] acetic acid (5.28 mg) was weighed in a glass vial, and methanol (1.0 mL) was then added to the vial, so that the aforementioned substance was dissolved in methanol. This glass vial was placed inside a larger glass vial filled with an appropriate amount of ethyl acetate, and the outside glass vial was then hermetically closed with a cap (vapor diffusion method). Three weeks later, it was found that a crystal was precipitated in the inside glass vial. Using the obtained single crystal (0.50×0.20×0.10 mm), an X-ray diffraction experiment was carried out employing R-AXIS RAPID II (Rigaku Corporation). Crystallographic data and structural analysis results are shown in Table 2, and atomic coordinate data are shown in Table 3. From these results, the absolute configuration of the title compound was specified.

TABLE 2

| | |
|---|---|
| Temperature | 100 K |
| Wavelength | 1.5418 Å |
| Crystalline system, Space group | Monoclinic system, P1 |
| Lattice constant | a = 10.5120 (7) Å |
| | b = 12.516 (1) Å |
| | c = 13.749 (1) Å |
| | α = 97.466(5) ° |
| | β = 91.637(4) ° |
| | γ = 100.997(5) ° |
| Volume | 1758.0 (3) Å$^3$ |
| Z value, Calculation density | 2, 1.338 g/cm$^3$ |
| Absorption coefficient | 15.193 cm$^{-1}$ |
| Crystal size | 0.50 × 0.20 × 0.10 mm |
| Maximum measurement 2θ | 136.4° |
| Total reflection number/ Unique reflection number | 16527/9183 [R (Intensity) = 0.0734] |
| Integrity | 95.80% |
| Phase determination | Direct method (SHELX97) |
| Precision method | least-squares method regarding F$^2$ |
| Data/parameter | 9183/915 |
| Goodness of fit | 1.12 |
| R value (total data) | 0.1193 |
| R value (I > 2σ (I)) | 0.0766 |
| Flack parameter | −0.01 (4) |
| Difference between maximum and minimum peaks | 0.57 and −0.55 e/Å$^3$ |

TABLE 3

| Atom | x | y | z | B (eq) |
|---|---|---|---|---|
| Cl1 | 0.4119(2) | 0.7216(2) | 0.2017(2) | 3.77(5) |
| Cl2 | 1.0126(2) | 0.1242(2) | 0.8268(2) | 3.88(5) |
| F1 | 0.6822(5) | 0.5796(5) | 0.5686(5) | 3.9(2) |
| F2 | 0.4752(5) | 0.5604(5) | 0.5619(5) | 4.1(2) |
| F3 | 0.5896(6) | 0.4670(5) | 0.4542(5) | 4.9(2) |
| F4 | 1.2722(6) | 0.3815(5) | 0.5804(5) | 4.4(2) |
| F5 | 1.3124(6) | 0.2702(5) | 0.4582(5) | 4.4(2) |
| F6 | 1.1195(5) | 0.3818(5) | 0.4727(5) | 4.6(2) |
| O1 | 0.1661(6) | 0.7584(5) | 0.6521(5) | 2.8(2) |
| O2 | −0.0333(6) | 0.6958(7) | 0.7021(5) | 3.7(2) |
| O3 | −0.0086(6) | 8.8003(5) | 0.4720(5) | 3.0(2) |
| O4 | 0.7323(6) | 0.0841(5) | 0.3764(5) | 3.1(2) |
| O5 | 0.5656(6) | 0.1418(6) | 0.3084(6) | 3.2(2) |
| O6 | 0.5324(6) | 0.0500(5) | 0.5451(5) | 3.0(2) |
| O7 | 0.2472(7) | 0.8855(6) | 0.0505(6) | 3.1(2) |
| O8 | 0.0090(6) | 0.9111(6) | 0.0180(5) | 3.2(2) |
| O9 | −0.0080(6) | 0.8224(6) | −0.1360(5) | 3.6(2) |
| O10 | 0.7535(6) | −0.0752(6) | 0.9744(5) | 2.8(2) |
| O11 | 0.5020(6) | −0.0893(5) | 0.9973(5) | 3.0(2) |
| O12 | 0.5310(6) | 0.0028(6) | 1.1492(5) | 3.4(2) |
| N1 | 0.2565(6) | 0.5984(6) | 0.3596(6) | 2.8(2) |
| N2 | 0.1600(7) | 0.7980(6) | 0.3731(6) | 2.8(2) |
| N3 | 0.1570(7) | 1.0437(7) | 0.1848(7) | 2.2(2) |
| N4 | 0.8943(6) | 0.2493(6) | 0.6668(6) | 2.7(2) |
| N5 | 0.7005(7) | 0.0555(7) | 0.6545(6) | 2.9(2) |
| N6 | 0.5917(6) | −0.2088(6) | 0.8249(6) | 2.4(2) |
| C1 | 0.4952(8) | 0.6468(8) | 0.3650(7) | 2.6(2) |
| C2 | 0.5120(8) | 0.7310(8) | 0.3065(7) | 2.8(2) |
| C3 | 0.6126(8) | 0.8222(8) | 0.3237(8) | 3.4(2) |
| C4 | 0.6979(8) | 0.8277(8) | 0.4026(8) | 3.1(2) |
| C5 | 0.6874(9) | 0.7435(9) | 0.4592(8) | 3.4(2) |
| C6 | 0.5857(8) | 0.6555(8) | 0.4412(8) | 2.8(2) |
| C7 | 0.5777(9) | 0.5675(8) | 0.5043(8) | 3.0(2) |

TABLE 3-continued

| Atom | x | y | z | B (eq) |
|---|---|---|---|---|
| C8 | 0.3753(8) | 0.5567(8) | 0.3399(8) | 3.1(2) |
| C9 | 0.1384(9) | 0.5269(8) | 0.3104(8) | 3.1(2) |
| C10 | 0.0233(8) | 0.5488(7) | 0.3708(7) | 2.6(2) |
| C11 | 0.0865(8) | 0.6378(7) | 0.4574(7) | 2.5(2) |
| C12 | 0.2265(8) | 0.6211(8) | 0.4627(7) | 2.4(2) |
| C13 | −0.0890(8) | 0.5750(9) | 0.3129(8) | 3.4(2) |
| C14 | 0.0145(8) | 0.6162(8) | 0.5494(7) | 2.7(2) |
| C15 | 0.0583(8) | 0.6970(8) | 0.6371(7) | 3.0(2) |
| C16 | 0.0769(7) | 0.7553(7) | 0.4356(7) | 2.2(2) |
| C17 | 0.1495(7) | 0.9031(7) | 0.3397(7) | 2.4(2) |
| C18 | 0.0375(8) | 0.8917(8) | 0.2626(7) | 2.8(2) |
| C19 | 0.0328(8) | 0.9990(7) | 0.2266(7) | 2.7(2) |
| C20 | 0.2679(8) | 1.0581(8) | 0.2568(7) | 2.7(2) |
| C21 | 0.2767(8) | 0.9531(8) | 0.2974(8) | 2.9(2) |
| C22 | 0.1485(8) | 1.1405(8) | 0.1405(8) | 2.9(2) |
| C23 | 0.2704(8) | 1.1993(8) | 0.0993(8) | 3.0(2) |
| C24 | 0.338(2) | 1.297(1) | 0.141(2) | 7.0(5) |
| C25 | 0.457(2) | 1.354(2) | 0.102(2) | 9.9(6) |
| C26 | 0.500(2) | 1.296(2) | 0.016(2) | 7.3(5) |
| C27 | 0.412(2) | 1.208(2) | −0.047(1) | 5.7(3) |
| C28 | 0.306(1) | 1.1450(9) | 0.0063(8) | 4.0(3) |
| C29 | 1.1103(8) | 0.2009(7) | 0.6631(7) | 2.5(2) |
| C30 | 1.0966(8) | 0.1154(8) | 0.7214(8) | 2.9(2) |
| C31 | 1.1552(9) | 0.0232(8) | 0.6983(8) | 3.1(2) |
| C32 | 1.2291(9) | 0.0162(8) | 0.6186(8) | 3.4(2) |
| C33 | 1.2512(8) | 0.1033(8) | 0.5625(8) | 3.0(2) |
| C34 | 1.1924(8) | 0.1936(8) | 0.5838(7) | 2.7(2) |
| C35 | 1.2235(8) | 0.2844(9) | 0.5233(8) | 3.3(2) |
| C36 | 1.0351(8) | 0.2910(8) | 0.6858(8) | 2.9(2) |
| C37 | 0.8142(8) | 0.3275(9) | 0.7115(8) | 3.3(2) |
| C38 | 0.6879(8) | 0.3027(9) | 0.6470(7) | 3.2(2) |
| C39 | 0.7039(8) | 0.2127(8) | 0.5636(7) | 2.6(2) |
| C40 | 0.8521(8) | 0.2246(8) | 0.5627(7) | 2.6(2) |
| C41 | 0.568(1) | 0.2831(9) | 0.7055(9) | 4.2(3) |
| C42 | 0.6434(8) | 0.2283(8) | 0.4665(7) | 2.7(2) |
| C43 | 0.6513(8) | 0.1407(8) | 0.3822(7) | 2.7(2) |
| C44 | 0.6374(8) | 0.0972(8) | 0.5857(7) | 2.9(2) |
| C45 | 0.6489(9) | −0.0532(8) | 0.6813(8) | 3.1(2) |
| C46 | 0.5365(8) | −0.0506(8) | 0.7504(8) | 2.9(2) |
| C47 | 0.4846(8) | −0.1669(8) | 0.7744(8) | 2.7(2) |
| C48 | 0.7044(8) | −0.2121(8) | 0.7584(7) | 2.6(2) |
| C49 | 0.7547(8) | −0.0983(8) | 0.7300(8) | 3.1(2) |
| C50 | 0.5404(9) | −0.3241(8) | 0.8498(8) | 3.4(2) |
| C51 | 0.6373(8) | −0.3622(8) | 0.9137(8) | 2.9(2) |
| C52 | 0.7227(9) | −0.4184(8) | 0.8752(8) | 3.4(2) |
| C53 | 0.828(1) | −0.4492(9) | 0.9352(8) | 3.6(2) |
| C54 | 0.821(2) | −0.410(2) | 1.043(1) | 6.6(4) |
| C55 | 0.741(2) | −0.351(2) | 1.080(1) | 12.3(9) |
| C56 | 0.626(1) | −0.3309(9) | 1.0217(8) | 3.4(2) |
| C57 | 0.1875(8) | 0.7110(8) | −0.0513(7) | 2.7(2) |
| C58 | 0.1750(9) | 0.6515(8) | 0.0274(8) | 3.3(2) |
| C59 | 0.175(1) | 0.5404(9) | 0.0160(8) | 3.6(2) |
| C60 | 0.188(1) | 0.484(1) | −0.0740(9) | 4.2(3) |
| C61 | 0.1991(9) | 0.5406(9) | −0.1553(8) | 3.4(2) |
| C62 | 0.1993(8) | 0.6546(8) | −0.1443(7) | 2.8(2) |
| C63 | 0.1880(8) | 0.8313(8) | −0.0423(7) | 2.8(2) |
| C64 | 0.0513(9) | 0.8567(8) | −0.0548(8) | 3.0(2) |
| C65 | 0.7830(8) | 0.1032(8) | 1.0765(7) | 2.6(2) |
| C66 | 0.8163(8) | 0.1620(8) | 1.1705(8) | 2.9(2) |
| C67 | 0.8731(9) | 0.2726(8) | 1.1802(9) | 3.6(2) |
| C68 | 0.898(1) | 0.3241(9) | 1.0990(9) | 4.1(3) |
| C69 | 0.866(1) | 0.2675(8) | 1.0071(9) | 3.9(3) |
| C70 | 0.8061(9) | 0.1562(8) | 0.9943(8) | 3.3(2) |
| C71 | 0.7217(7) | −0.0192(7) | 1.0641(7) | 2.3(2) |
| C72 | 0.5727(8) | −0.0338(7) | 1.0709(7) | 2.6(2) |
| H2 | −0.0067 | 0.7391 | 0.7396 | 0.06 |
| H2A | 0.2223 | 0.7565 | 0.3396 | 3.76 |
| H3 | 0.1623 | 1.0065 | 0.1437 | 0.00 |
| H3A | 0.6220 | 0.8783 | 0.2825 | 4.05 |
| H4 | 0.7652 | 0.8907 | 0.4185 | 3.78 |
| H5 | 0.5766 | 0.0892 | 0.2461 | 5.51 |
| H5A | 0.7659 | 0.0835 | 0.6906 | 12.08 |
| H5B | 0.7508 | 0.7463 | 0.5106 | 4.03 |
| H6 | 0.6367 | −0.1489 | 0.8990 | 2.67 |
| H7 | 0.3077 | 0.8856 | 0.0380 | 3.75 |
| H8A | 0.3734 | 0.5262 | 0.2697 | 3.69 |
| H8B | 0.3797 | 0.4966 | 0.3794 | 3.69 |
| H9A | 0.1455 | 0.4488 | 0.3069 | 3.71 |
| H9B | 0.1262 | 0.5436 | 0.2427 | 3.71 |
| H10 | 0.8221 | −0.0844 | 0.9746 | 4.22 |
| H10A | −0.0108 | 0.4803 | 0.3996 | 3.10 |
| H12A | 0.2853 | 0.6880 | 0.4961 | 2.88 |
| H12B | 0.2342 | 0.5585 | 0.4982 | 2.88 |
| H13A | −0.1584 | 0.5862 | 0.3569 | 4.09 |
| H13B | −0.122 | 0.5137 | 0.2609 | 4.09 |
| H13C | −0.0593 | 0.6419 | 0.2833 | 4.09 |
| H14A | −0.0789 | 0.6140 | 0.5351 | 3.20 |
| H14B | 0.0233 | 0.5427 | 0.5647 | 3.20 |
| H17 | 0.1337 | 0.9548 | 0.3979 | 2.85 |
| H18A | 0.0482 | 0.8368 | 0.2063 | 3.33 |
| H18B | −0.0457 | 0.8647 | 0.2917 | 3.33 |
| H19A | −0.0388 | 0.9882 | 0.1757 | 3.20 |
| H19B | 0.0151 | 1.0524 | 0.2818 | 3.20 |
| H20A | 0.2592 | 1.1154 | 0.3116 | 3.21 |
| H20B | 0.3493 | 1.0837 | 0.2248 | 3.21 |
| H21A | 0.3472 | 0.9685 | 0.3495 | 3.52 |
| H21B | 0.2988 | 0.8993 | 0.2444 | 3.52 |
| H22A | 0.0790 | 1.1267 | 0.0875 | 3.49 |
| H22B | 0.1224 | 1.1994 | 0.1915 | 3.49 |
| H24 | 0.3077 | 1.3317 | 0.1995 | 8.43 |
| H25A | 0.4432 | 1.4261 | 0.0872 | 11.90 |
| H25B | 0.5279 | 1.3681 | 0.1545 | 11.90 |
| H26A | 0.5735 | 1.2645 | 0.0373 | 8.80 |
| H26B | 0.5347 | 1.3518 | −0.0262 | 8.80 |
| H27A | 0.4837 | 1.1565 | −0.0789 | 6.89 |
| H27B | 0.3722 | 1.2405 | −0.0992 | 6.89 |
| H28A | 0.2272 | 1.1243 | −0.0386 | 4.75 |
| H28B | 0.3323 | 1.0760 | 0.0189 | 4.75 |
| H31 | 1.1431 | −0.034 | 0.7384 | 3.77 |
| H32 | 1.2652 | −0.0472 | 0.6012 | 4.05 |
| H33 | 1.3070 | 0.1005 | 0.5094 | 3.60 |
| H36A | 1.0528 | 0.3233 | 0.7557 | 3.51 |
| H36B | 1.0641 | 0.3497 | 0.6450 | 3.51 |
| H37A | 0.8595 | 0.4045 | 0.7114 | 3.99 |
| H37B | 0.7963 | 0.3157 | 0.7800 | 3.99 |
| H38 | 0.6850 | 0.3701 | 0.6158 | 3.84 |
| H40A | 0.8762 | 0.1555 | 0.5325 | 3.13 |
| H40B | 0.8907 | 0.2850 | 0.5264 | 3.13 |
| H41A | 0.5676 | 0.3482 | 0.7535 | 5.00 |
| H41B | 0.5686 | 0.2194 | 0.7399 | 5.00 |
| H41C | 0.4905 | 0.2692 | 0.6609 | 5.00 |
| H42A | 0.5509 | 0.2312 | 0.4752 | 3.22 |
| H42B | 0.6866 | 0.3002 | 0.4490 | 3.22 |
| H45 | 0.6152 | −0.104 | 0.6199 | 3.76 |
| H46A | 0.5675 | −0.0005 | 0.8118 | 3.42 |
| H46B | 0.4661 | −0.0228 | 0.7185 | 3.42 |
| H47A | 0.4112 | −0.1657 | 0.8178 | 3.21 |
| H47B | 0.4525 | −0.2167 | 0.7130 | 3.21 |
| H48A | 0.6755 | −0.2652 | 0.6985 | 3.10 |
| H48B | 0.7751 | −0.2369 | 0.7930 | 3.10 |
| H49A | 0.7912 | −0.0473 | 0.7896 | 3.69 |
| H49B | 0.8254 | −0.1025 | 0.6845 | 3.69 |
| H50A | 0.4590 | −0.3244 | 0.8843 | 4.12 |
| H50B | 0.5201 | −0.3762 | 0.7882 | 4.12 |
| H52 | 0.7168 | −0.4404 | 0.8061 | 4.05 |
| H53A | 0.9139 | −0.4161 | 0.9129 | 4.34 |
| H53B | 0.8202 | −0.53 | 0.9249 | 4.34 |
| H54A | 0.8072 | −0.4773 | 1.0754 | 7.89 |
| H54B | 0.9094 | −0.369 | 1.0655 | 7.89 |
| H55A | 0.7935 | −0.2778 | 1.1053 | 14.82 |
| H55B | 0.7061 | −0.3841 | 1.1375 | 14.82 |
| H56A | 0.5454 | −0.3744 | 1.0427 | 4.09 |
| H56B | 0.6211 | −0.2522 | 1.0351 | 4.09 |
| H58 | 0.1659 | 0.6884 | 0.0910 | 4.00 |
| H59 | 0.1666 | 0.5025 | 0.0717 | 4.35 |
| H60 | 0.1888 | 0.4079 | −0.0811 | 5.05 |
| H61 | 0.2067 | 0.5022 | −0.2185 | 4.06 |
| H62 | 0.2074 | 0.6927 | −0.2 | 3.35 |
| H63 | 0.2413 | 0.8619 | −0.095 | 3.35 |
| H66 | 0.8000 | 0.1264 | 1.2272 | 3.43 |
| H67 | 0.8947 | 0.3130 | 1.2438 | 4.38 |
| H68 | 0.9388 | 0.3996 | 1.1065 | 4.95 |
| H69 | 0.8844 | 0.3040 | 0.9512 | 4.65 |
| H70 | 0.7817 | 0.1176 | 0.9303 | 3.92 |
| H71 | 0.7565 | −0.0519 | 1.1192 | 2.75 |

The following test examples were carried out to examine the pharmacological effects of the compound (1).

Test Example 1

Inhibition of Cell Migration in Fractalkine-Induced Chemotaxis Assay (1) Method

The inhibitory effects of the example compounds on fractalkine-induced cell migration were examined using CX3CR1-transfected B300 cells After equilibrating the Transwell plate (24-well clusters, pore size: 5 μm, manufactured by Corning Incorporated), a fractalkine solution (0.3 nM, manufactured by R&D Systems, Inc.) was added to the lower wells. CX3CR1-expressing B300 cells which were preincubated with the test compound (0.001, 0.003, 0.01 or 0.03 μM) for 30 minutes were placed in the upper layer wells, followed by incubation under the condition of 5% $CO_2$ for 3.5 hours at 37° C. The number of cells migrated to the lower wells was evaluated using CellTiter (manufactured by Promega Corporation).

The inhibitory rate of the test compound on fractalkine-induced cell migration was calculated by the following formula, where [A] is the number of migrated cells in the presence of both fractalkine and the test compound, [B] is the number of migrated cells in the presence of fractalkine and in the absence of the test compound, and [C] is the number of migrated cells in the absence of both fractalkine and the test compound; the 50% inhibitory concentration ($IC_{50}$) was calculated based on the inhibitory rate.

Inhibitory rate (%)=[1−{(A−C)/(B−C)}]×100

(2) Results

As a result of the present test example, the $IC_{50}$ of the compound (1) was found to be 4 nM.

Test Example 2

Amelioration of Body Weight Loss in T Cell Transfer-Induced Colitis Model (1) Method By using colitis-induced SCID mice in which CD4-positive, CD45RB-high cells isolated from BALB/c mice splenocytes were injected, the efficacy of the example compounds was evaluated by the body weight changes. The experiment was performed over 31 days. On Day 1, CD4-positive, CD45RB-high cells isolated from the spleen of BALB/c mice ($5\times10^5$ cells/mouse) were intravenously administered to SCID mice. From Day 16 to 31, the example compound was orally administered to the SCID mice once a day, followed by measuring body weights of all animals on Day 19, 22, 24, 26, 29 and 31.

The efficacy was evaluated by body weight changes on Day 19, 22, 24, 26, 29 or 31. The body weight change (%) was determined by the formula shown below, where [A] is the body weight on Day 16, and [B] is the body weight on each day of body weight measurement (Day 19, 22, 24, 26, 29 or 31).

body weight change (%)=B/A×100

(2) Results

Figure 6:
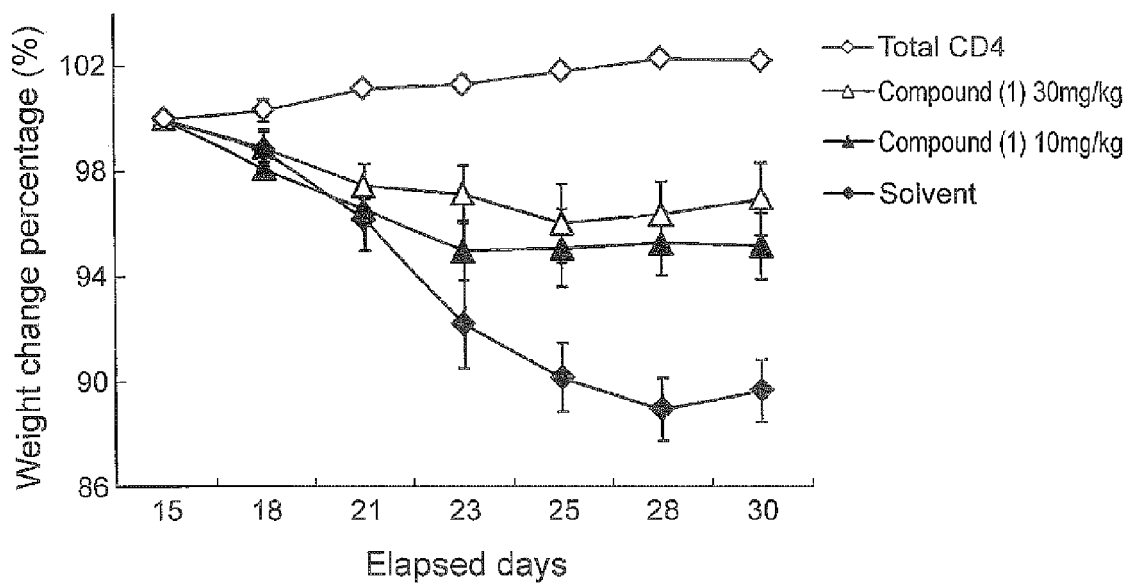
FIG. 6 is a graph showing the weight reduction-suppressing effect of 2-[(3S,4R)-1-{[2-chloro-6-(trifluoromethyl)phenyl]methyl}-3-{[1-(cyclohex-1-en-1-ylmethyl) piperidin-4-yl]carbamoyl}-4-methylpyrrolidin-3-yl]acetic acid on a T cell transfer colitis model. The abscissa indicates days elapsed, provided that the day at which CD4-positive CD45RB highly positive cells ($5 \times 10^5$ cells/mouse) collected from the spleen of a BALB/c mouse were intravenously administered to an SCID mouse was defined as day 0.

The results are shown in FIG. 6. The abscissa in the figures indicates the number of days elapsed, where the day on which CD4-positive, CD45RB-high cells isolated from the spleen of BALB/c mice ($5\times10^5$ cells/mouse) were intravenously administered to SCID mice is Day 0.

The invention claimed is:

1. A crystal of an organic carboxylic acid salt of 2-[(3S,4R)-1-{[2-chloro-6-(trifluoromethyl)phenyl]methyl}-3-{[1-(cyclohex-1-en-1-ylmethyl)piperidin-4-yl]carbamoyl}-4-methylpyrrolidin-3-yl]acetic acid, wherein the organic carboxylic acid is L-mandelic acid.

2. The crystal according to claim 1, which is characterized by having a diffraction peak at a diffraction angle (2θ±0.2°) of 7.2° in powder X-ray diffractometry.

3. The crystal according to claim 2, which is characterized by having further diffraction peaks at diffraction angles (2θ±0.2°) of 14.4° and 15.7° in powder X-ray diffractometry.

4. The crystal according to claim 3, which is characterized by having further diffraction peaks at diffraction angles (2θ±0.2°) of 10.3° and 23.5° in powder X-ray diffractometry.

5. The crystal according to claim 4, which is characterized by having further diffraction peaks at diffraction angles (2θ±0.2°) of 12.9°, 14.9°, 17.2°, 20.1° and 24.7° in powder X-ray diffractometry.

6. The crystal according to claim 1, which is characterized by having peaks at chemical shifts (±0.5 ppm) of 14.1, 52.9, 75.2, 144.7 and 174.0 in $^{13}C$ solid state NMR spectrum.

* * * * *